(12) United States Patent
Fischer et al.

(10) Patent No.: US 8,383,853 B2
(45) Date of Patent: Feb. 26, 2013

(54) METHOD FOR PREPARING 2,6-DIETHYL-4-METHYLPHENYLACETIC ACID

(75) Inventors: Reiner Fischer, Monheim (DE); Stefan Lehr, Liederbach (DE); Mark Wilhelm Drewes, Langenfeld (DE); Dieter Feucht, Eschborn (DE); Olga Malsam, Rosrath (DE); Guido Bojack, Wiesbaden (DE); Christian Arnold, Langenfeld (DE); Thomas Auler, Leichlingen (DE); Jeffrey Martin Hills, Idstein (DE); Heinz Kehne, Hofheim (DE); Chris Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 349 days.

(21) Appl. No.: 12/821,831

(22) Filed: Jun. 23, 2010

(65) Prior Publication Data
US 2010/0261934 A1    Oct. 14, 2010

Related U.S. Application Data

(62) Division of application No. 11/666,870, filed as application No. PCT/EP2005/011343 on Oct. 21, 2005, now abandoned.

(30) Foreign Application Priority Data

Nov. 4, 2004  (DE) .......................... 10 2004 053 191

(51) Int. Cl.
*C07C 229/00*  (2006.01)
(52) U.S. Cl. ........................................ 562/496
(58) Field of Classification Search .................. 562/496
See application file for complete search history.

(56) References Cited

U.S. PATENT DOCUMENTS

| | | | |
|---|---|---|---|
| 4,021,224 A | 5/1977 | Pallos et al. | |
| 4,186,130 A | 1/1980 | Teach | |
| 4,623,727 A | 11/1986 | Hübele | |
| 4,639,266 A | 1/1987 | Heubach et al. | |
| 4,881,966 A | 11/1989 | Nyffeler et al. | |
| 4,891,057 A | 1/1990 | Sohn et al. | |
| 4,902,340 A | 2/1990 | Hubele | |
| 4,925,868 A | 5/1990 | Terao et al. | |
| 4,985,063 A | 1/1991 | Fischer et al. | |
| 5,045,560 A | 9/1991 | Fischer et al. | |
| 5,116,836 A | 5/1992 | Fischer et al. | |
| 5,225,434 A | 7/1993 | Bertram et al. | |
| 5,258,527 A | 11/1993 | Krauskopf et al. | |
| 5,314,863 A | 5/1994 | Löher et al. | |
| 5,380,852 A | 1/1995 | Schütze et al. | |
| 5,401,700 A | 3/1995 | Sohn et al. | |
| 5,407,897 A | 4/1995 | Cary et al. | |
| 5,462,913 A | 10/1995 | Fischer et al. | |
| 5,504,057 A | 4/1996 | Fischer et al. | |
| 5,516,750 A | 5/1996 | Willms et al. | |
| 5,567,671 A | 10/1996 | Fischer et al. | |
| 5,589,469 A | 12/1996 | Fischer et al. | |
| 5,622,917 A | 4/1997 | Fischer et al. | |
| 5,683,965 A | 11/1997 | Bachmann et al. | |
| 5,700,758 A | 12/1997 | Rösch et al. | |
| 5,739,079 A | 4/1998 | Holdgrün et al. | |
| 5,811,374 A | 9/1998 | Bertram et al. | |
| 5,830,826 A | 11/1998 | Fischer et al. | |
| 6,114,374 A | 9/2000 | Lieb et al. | |
| 6,133,296 A | 10/2000 | Lieb et al. | |
| 6,140,358 A | 10/2000 | Lieb et al. | |
| 6,200,932 B1 | 3/2001 | Fischer et al. | |
| 6,235,680 B1 | 5/2001 | Ziemer et al. | |
| 6,251,827 B1 | 6/2001 | Ziemer et al. | |
| 6,251,830 B1 | 6/2001 | Fischer et al. | |
| 6,316,486 B1 | 11/2001 | Lieb et al. | |
| 6,358,887 B1 | 3/2002 | Fischer et al. | |
| 6,417,370 B1 | 7/2002 | Lieb et al. | |
| 6,451,843 B1 | 9/2002 | Lieb et al. | |
| 6,458,965 B1 | 10/2002 | Lieb et al. | |
| 6,472,419 B1 | 10/2002 | Fischer et al. | |

(Continued)

FOREIGN PATENT DOCUMENTS

CA    2 368 827 A1    12/2000
CA    2 492 096 A1     1/2004

(Continued)

OTHER PUBLICATIONS

Lee et al. (J. Am. Chem. Soc. 2001, 123; 8410-8411).*
Jorgensen et al. (J. Am. Chem. Soc. 2002, 124; 12557-12565).*
Moradi et al. (J. Am. Chem. Soc. 2001, 123; 7996-8002).*
Campa et al. (Nouveau Journal de Chimie (1985), 9(7); p. 493-498).*
Lee, S., et al., "Palladium-Catalyzed α-Arylation of Esters and Protected Amino Acids," *J. Am. Chem. Soc.* 123:8410-8411, American Chemical Society (2001).
Lloyd-Jones, G.C., "Palladium-Catalyzed α-Arylation of Esters: Ideal New Methodology for Discovery Chemistry," *Angew. Chem. Int. Ed.* 41:953-956, Wiley-VCH Verlag GmbH (2002).
Moradi, W.A., and Buchwald, S.L., "Palladium-Catalyzed α-Arylation of Esters," *J. Am. Chem. Soc.* 123:7996-8002, American Chemical Society (2001).

(Continued)

*Primary Examiner* — Yong Chu
*Assistant Examiner* — Valerie Rodriguez-Garcia
(74) *Attorney, Agent, or Firm* — Sterne, Kessler, Goldstein & Fox, P.L.L.C.

(57) ABSTRACT

The invention relates to novel 2,6-diethyl-4-methylphenyl-substituted tetramic acid derivatives of the formula (I)

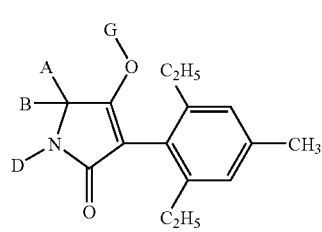

(I)

in which A, B, D and G are as defined above, to a plurality of processes and intermediates for their preparation and to their use as pesticides and/or herbicides, and also to selectively herbicidal compositions comprising, firstly, the 2,6-diethyl-4-methylphenyl-substituted tetramic acid derivatives of the formula (I) and, secondly, at least one crop plant tolerance promoter compound.

3 Claims, No Drawings

U.S. PATENT DOCUMENTS

| | | |
|---|---|---|
| 6,511,942 B1 | 1/2003 | Turberg et al. |
| 6,589,976 B1 | 7/2003 | Fischer et al. |
| 6,608,211 B1 | 8/2003 | Hagemann et al. |
| 6,642,180 B1 | 11/2003 | Fischer et al. |
| 6,861,391 B1 | 3/2005 | Fischer et al. |
| 6,894,005 B1 | 5/2005 | Maetzke et al. |
| 2002/0072617 A1 | 6/2002 | Hagemann et al. |
| 2003/0171220 A1 | 9/2003 | Ziemer et al. |
| 2003/0216260 A1 | 11/2003 | Ruther et al. |
| 2005/0054535 A1 | 3/2005 | Fischer et al. |
| 2006/0160847 A1 | 7/2006 | Fischer et al. |
| 2006/0166829 A1 | 7/2006 | Fischer et al. |
| 2007/0015825 A1 | 1/2007 | Fischer et al. |
| 2007/0129252 A1 | 6/2007 | Fischer et al. |
| 2007/0225167 A1 | 9/2007 | Fischer et al. |
| 2007/0244007 A1 | 10/2007 | Fischer et al. |
| 2007/0254949 A1 | 11/2007 | Bretschneider et al. |
| 2007/0265266 A1 | 11/2007 | Fischer et al. |
| 2007/0270416 A1 | 11/2007 | Funke et al. |
| 2007/0276023 A1 | 11/2007 | Fischer et al. |
| 2007/0298969 A1 | 12/2007 | Fischer et al. |
| 2008/0027114 A1 | 1/2008 | Funke et al. |
| 2008/0167188 A1 | 7/2008 | Fischer et al. |
| 2008/0188371 A1 | 8/2008 | Fischer et al. |
| 2008/0200499 A1 | 8/2008 | Fischer et al. |
| 2008/0220973 A1 | 9/2008 | Fischer et al. |
| 2008/0287435 A1 | 11/2008 | Fischer et al. |
| 2008/0305955 A1 | 12/2008 | Bretschneider et al. |
| 2008/0318776 A1 | 12/2008 | Fischer et al. |
| 2009/0012100 A1 | 1/2009 | Fischer et al. |
| 2009/0012152 A1 | 1/2009 | Fischer et al. |
| 2009/0029858 A1 | 1/2009 | Fischer et al. |
| 2009/0215624 A1 | 8/2009 | Fischer et al. |
| 2009/0281157 A1 | 11/2009 | Fischer et al. |
| 2009/0298828 A1 | 12/2009 | Fischer et al. |

FOREIGN PATENT DOCUMENTS

| | | | |
|---|---|---|---|
| CA | 2 497 074 | A1 | 3/2004 |
| CA | 2 518 620 | A1 | 9/2004 |
| CA | 2 544 537 | A1 | 5/2005 |
| CA | 2 544 548 | A1 | 5/2005 |
| CA | 2 546 815 | A1 | 6/2005 |
| CA | 2 546 817 | A1 | 6/2005 |
| EP | 0 346 620 | A1 | 12/1989 |
| GB | 1 411 866 | | 10/1975 |
| GB | 2 266 888 | A | 11/1993 |
| WO | WO 94-29268 | A1 | 12/1994 |
| WO | WO 01/74770 | * | 10/2001 |

OTHER PUBLICATIONS

Schmierer, R., and Mildenberger, H., "Cyclisierung von N-Acylalanin- und N-Acylglycinestern," *Liebigs Ann. Chem.* 6:1095-1098, VCH Verlagsgesellschaft mbH (1985).

Suzuki, S., et al., "Studies on antiviral agents. IV. Biological activity of tenuazonic acid derivatives," *Chem. Pharm, Bull.* 15:1120-1122, Pharmaceutical Society of Japan (1967).

Dialog File 351, Accession No. 4963457, Derwent WPI English language abstract for EP 0 346 620 A (listed on accompanying form PTO/SB/08A as document FPI) (2004).

Database CAPLUS on STN, Chemical Accession No. 1985:437721 English language abstract, Schmierer, R., and Mildenberger, H., "Cyclization of N-acylalanine and N-acylglycine esters," *Liebigs Ann. Chem.* 5:1095-1098, Verlag Chemie (1985) (Abstract for document NPL4).

International Search Report for International Application No. PCT/EP2005/011343, European Patent Office, Netherlands, mailed on Nov. 4, 2006.

Office Action for U.S. Appl. No. 08/140,635, filed Oct. 21, 1993, inventors Fisher, R., et al., mailed on Nov. 15, 1994.

Office Action for U.S. Appl. No. 10/578,900, filed Mar. 8, 2007, inventors Fisher, R., et al., mailed on Jun. 22, 2009.

Office Action for U.S. Appl. No. 10/578,900, filed Mar. 8, 2007, inventors Fisher, R., et al., mailed on Sep. 30, 2008.

* cited by examiner

METHOD FOR PREPARING 2,6-DIETHYL-4-METHYLPHENYLACETIC ACID

This is a Divisional Application of application Ser. No. 11/666,870, filed Mar. 24, 2008, which is the U.S. National Phase of International Application No. PCT/EP2005/011343, filed Oct. 10, 2005, which claims priority to DE 102004053191.9, filed Nov. 4, 2004, each of which is wholly incorporated by reference herein.

The invention relates to novel 2,6-diethyl-4-methylphenyl-substituted tetramic acid derivatives, to a plurality of processes for their preparation and to their use as pesticides and/or herbicides. Moreover, the invention relates to novel selective herbicidal active compound combinations comprising, firstly, the 2,6-diethyl-4-methylphenyl-substituted tetramic acid derivatives and, secondly, a crop plant tolerance promoter compound, which combinations can be used with particularly good results for the selective control of weeds in various crops of useful plants.

Pharmaceutical properties of 3-acylpyrrolidine-2,4-diones are described in the prior art (S. Suzuki et al. Chem. Pharm. Bull. 15 1120 (1967)). Furthermore, R. Schmierer and H. Mildenberger (Liebigs Ann. Chem. 1985, 1095) synthesize N-phenylpyrrolidine-2,4-diones. A biological activity of these compounds has not been described.

EP-A-0 262 399 and GB-A-2 266 888 disclose compounds of a similar structure (3-arylpyrrolidine-2,4-diones); however, a herbicidal, insecticidal or acaricidal action of these compounds is not known. Known to have a herbicidal, insecticidal or acaricidal action are unsubstituted, bicyclic 3-arylpyrroli-dine-2,4-dione derivatives (EP-A-355 599 and EP-A-415 211), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073), and also 1H-arylpyrrolidine dione derivatives (EP-A-456 063, EP-A-521 334, EP-A-596 298, EP-A-613 884, EP-A-613 885, WO 94/01 997, WO 95/26954, WO 95/20 572, EP-A 0 668 267, WO 96/25 395, WO 96 35 664, WO 97/01 535, WO 97/02 243, WO 97/36 868, WO 97/43275, WO/98/05638, WO 98/06721, WO 98/25928, WO 99/16748, WO 99/24437, WO 99/43649, WO 99/48869, WO 99/55673, WO 01/09092, WO 01/17 972, WO 01/23354, WO 01/74770, WO 03/013249, WO 2004/007448, DE-A-10 239 479, WO 04/065336, WO 04/080962, WO 04/111042, WO 05/044791, WO 05/044796, WO 05/048710, WO 05/049569, DE-A-04 001 433).

However, the efficacy and activity spectrum of these compounds, in particular at low application rates and concentrations, are not always satisfactory. Furthermore, the compatibility of these compounds with crops is not always sufficient.

This invention now provides novel compounds of the formula (I).

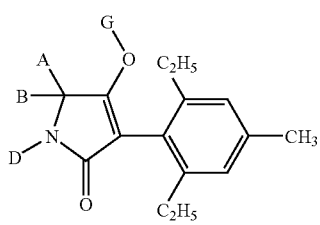
(I)

in which
A represents hydrogen, represents in each case optionally halogen-substituted alkyl, alkenyl, alkoxyalkyl or alkylthioalkyl or represents optionally substituted cycloalkyl,
B represents hydrogen, alkyl or alkoxyalkyl, or
A and B together with the carbon atom to which they are attached represent a saturated or unsaturated $C_3$-$C_8$-ring which optionally contains at least one heteroatom and which is optionally substituted and
D represents hydrogen,
or
A represents hydrogen or alkyl,
B represents hydrogen and
D represents an optionally substituted radical from the group consisting of alkyl, alkenyl, alkynyl, alkoxyalkyl, alkylthioalkyl or optionally cycloalkyl, or
A and D together with the atoms to which they are attached represent a saturated or unsaturated cycle which optionally contains at least one oxygen or sulfur atom in the A,D moiety or which is optionally substituted by alkyl, alkoxy or haloalkyl and
G represents one of the groups

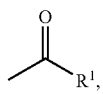
(b)

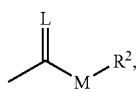
(c)

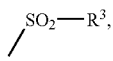
(d)

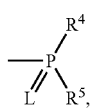
(e)

E or
(f)

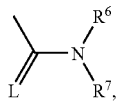
(g)

in which
E represents a metal ion equivalent or an ammonium ion,
L represents oxygen or sulfur,
M represents oxygen or sulfur,
$R^1$ represents in each case optionally substituted primary or secondary alkyl, alkenyl, alkoxy-alkyl, alkylthioalkyl or polyalkoxyalkyl or represents in each case optionally halogen-, alkyl- or alkoxy-substituted cycloalkyl or heterocyclyl or represents in each case optionally substituted phenyl or hetaryl,
$R^2$ represents in each case optionally halogen-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen-substituted alkyl, cycloalkyl, alkenyl, alkoxy, alkoxyalkyl, represent in each case optionally substituted phenyl or benzyl or together with the N atom to which they are attached form an optionally substituted cycle which optionally contains oxygen or sulfur.

Depending inter alia on the nature of the substitutents, the compounds of the formula (I) can be present as geometrical and/or optical isomers or isomer mixtures of varying composition which, if appropriate, may be separated in a customary manner. The present invention provides both the pure isomers and the isomer mixtures, their preparation and use, and compositions comprising them. However, for the sake of simplicity, hereinbelow only compounds of the formula (I) are referred to, although what is meant are both the pure compounds and, if appropriate, also mixtures having varying proportions of isomeric compounds.

Including the meanings (b), (c), (d), (e), (f) and (g) of group G, the following principal structures (I-b) to (I-g) result:

(I-b):

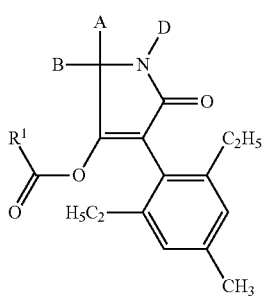

(I-c):

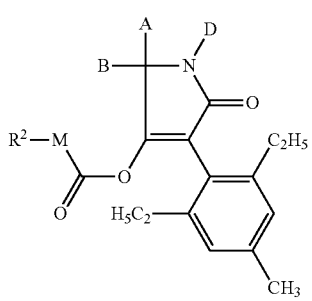

(I-d):

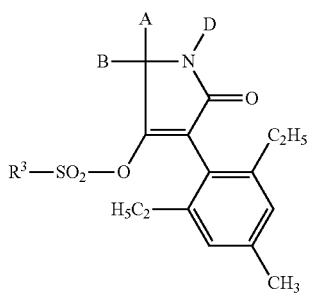

(I-e):

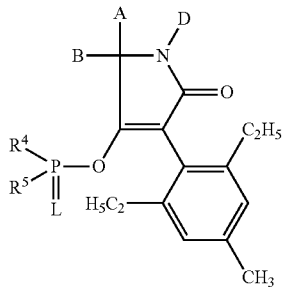

(I-f):

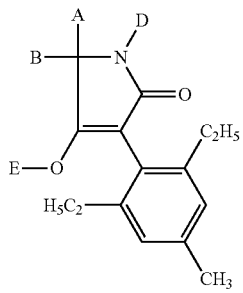

(I-g):

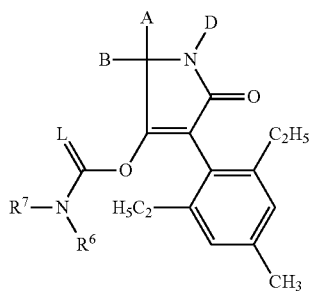

in which
A, B, D, E, L, M, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) compounds of the formula (I-b) shown above in which A, B, D and $R^1$ are as defined above are obtained when compounds of the formula (I-a)

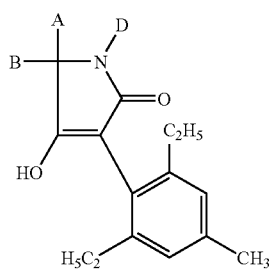

(I-a)

in which
A, B and D are as defined above
are reacted

α) with acid halides of the formula (II)

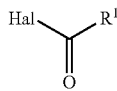
(II)

in which
R¹ is as defined above and
Hal represents halogen (in particular chlorine or bromine)
or
β) with carboxylic anhydrides of the formula (III)

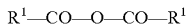
(III)

in which
R¹ is as defined above,
if appropriate in the presence of a diluent and if appropriate in the presence of an acid binder.

(C) Compounds of the formula (I-c) shown above in which A, B, D, R² and M are as defined above and L represents oxygen are obtained when compounds of the formula (I-a) shown above in which A, B and D are as defined above are in each case reacted
with chloroformic esters or chloroformic thioesters of the formula (IV)

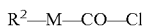
(IV)

in which
R² and M are as defined above,
if appropriate in the presence of a diluent and if appropriate in the presence of an acid binder.

(D) Compounds of the formula (I-c) shown above in which A, B, D, R² and M are as defined above and L represents sulfur are obtained when compounds of the formula (I-a) shown above in which A, B and D are as defined above are in each case
α) reacted with chloromonothioformic esters or chlorodithioformic esters of the formula (V)

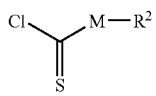
(V)

in which
M and R² are as defined above,
if appropriate in the presence of a diluent and if appropriate in the presence of an acid binder,
or
β) reacted with carbon disulfide and then with compounds of the formula (VI)

(VI)

in which
R² is as defined above and
Hal represents chlorine, bromine or iodine,
if appropriate in the presence of a diluent and if appropriate in the presence of a base.

(E) Compounds of the formula (I-d) shown above in which A, B, D and R³ are as defined above are obtained when compounds of the formula (I-a) shown above in which A, B and D are as defined above are in each case reacted
with sulfonyl chlorides of the formula (VII)

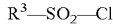
(VII)

in which
R³ is as defined above,
if appropriate in the presence of a diluent and if appropriate in the presence of an acid binder.

(F) Compounds of the formula (I-e) shown above in which A, B, D, L, R⁴ and R⁵ are as defined above are obtained when compounds of the formula (I-a) shown above in which A, B and D are as defined above are in each case reacted
with phosphorus compounds of the formula (VIII)

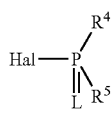
(VIII)

in which
L, R⁴ and R⁵ are as defined above and
Hal represents halogen (in particular chlorine or bromine),
if appropriate in the presence of a diluent and if appropriate in the presence of an acid binder.

(G) Compounds of the formula (I-f) shown above in which A, B, D and E are as defined above are obtained when compounds of the formulae (I-a) in which A, B and D are as defined above are in each case reacted
with metal compounds or amines of the formulae (IX) or (X)

(IX)

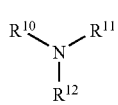
(X)

in which
Me represents a mono- or divalent metal (preferably an alkali metal or alkaline earth metal, such as lithium, sodium, potassium, magnesium or calcium),
t represents the number 1 or 2 and
R¹⁰, R¹¹, R¹² independently of one another represent hydrogen or alkyl (preferably $C_1$-$C_8$-alkyl),
if appropriate in the presence of a diluent.

(H) Compounds of the formula (I-g) shown above in which A, B, D, L, R⁶ and R⁷ are as defined above are obtained when compounds of the formula (I-a) shown above in which A, B and D are as defined above are in each case
α) reacted with isocyanates or isothiocyanates of the formula (XI)

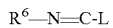
(XI)

in which
R⁶ and L are as defined above,
if appropriate in the presence of a diluent and if appropriate in the presence of a catalyst, or
β) reacted with carbamoyl chlorides or thiocarbamoyl chlorides of the formula (XII)

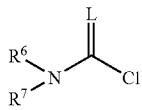

in which

L, $R^6$ and $R^7$ are as defined above, if appropriate in the presence of a diluent and if appropriate in the presence of an acid binder.

Furthermore, it has been found that the novel compounds of the formula (I) have very good activity as pesticides, preferably as insecticides and/or acaricides, and/or as herbicides.

Surprisingly, it has now been found that certain substituted cyclic ketoenols, when employed together with the crop plant tolerance promoter compounds (safeners/antidotes) described later on, are extremely good at preventing damage to the crop plants and can be used with particular advantage as broad-spectrum combination products for the selective control of unwanted plants in crops of useful plants, such as, for example, in cereals, but also in maize, soybeans and rice.

The invention also provides selective herbicidal compositions comprising an effective amount of an active compound combination comprising, as components, a') at least one substituted cyclic ketoenol of the formula (I) in which A, B, D and G are as defined above
or
b') at least one substituted cyclic ketoenol of the formula (I-a)

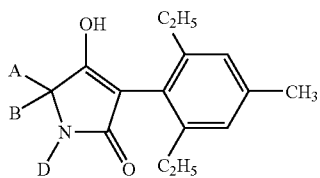

(I-a)

in which

A represents hydrogen, $C_2$-$C_{10}$-alkyl, $C_1$-$C_6$-haloalkyl, represents in each case optionally halogen-substituted alkenyl, alkoxyalkyl or alkylthioalkyl or represents optionally substituted cycloalkyl, B represents hydrogen, alkyl or alkoxyalkyl, or A and B together with the carbon atom to which they are attached represent a saturated or unsaturated $C_3$-$C_8$-ring which is substituted by alkyl, alkoxy or haloalkyl or represent a $C_5$-$C_8$-ring which contains at least one heteroatom and which is optionally substituted, and D represents hydrogen Or A represents hydrogen or alkyl, B represents hydrogen and D represents an optionally substituted radical from the group consisting of $C_2$-$C_{10}$-alkyl, alkenyl, alkynyl, alkoxyalkyl, alkylthioalkyl or optionally substituted cycloalkyl, or A and D together with the atoms to which they are attached represent a saturated or unsaturated cycle which optionally contains at least one oxygen or sulfur atom in the A,D-moiety or which is optionally substituted by alkyl, alkoxy or haloalkyl, and (c') at least one crop plant tolerance promoter compound from the following group of compounds:

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxy-acetate (cloquintocet-mexyl-cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl-cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloro-acetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl-cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl-cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxy-malonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxy-benzophenone, 1-bromo-4-chloromethylsulfonylbenzene, 1-[4-(N-2-methoxybenzoylsulfamoyl)-phenyl]-3-methylurea (also known as N-(2-methoxybenzoyl)-4-

[(methylaminocarbonyl)-amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)benzenesulfonamide, and/or one of the following compounds, defined by general formulae,
of the general formula (IIa)

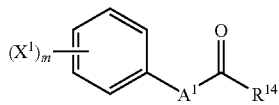

(IIa)

or of the general formula (IIb)

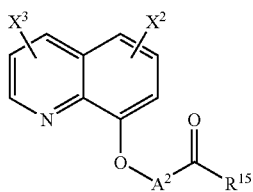

(IIb)

or of the formula (IIc)

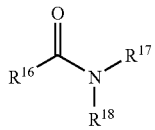

(IIc)

where
m represents a number 0, 1, 2, 3, 4 or 5,
$A^1$ represents one of the divalent heterocyclic groupings shown below

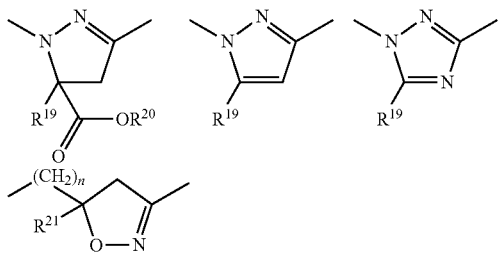

n represents a number 0, 1, 2, 3, 4 or 5,
$A^2$ represents optionally $C_1$-$C_4$-alkyl- and/or $C_1$-$C_4$-alkoxycarbonyl- and/or $C_1$-$C_4$-alkenyloxy-carbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)amino, $R^{16}$ represents in each case optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carboxycle,
$R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl,
$R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
and/or the following compounds, defined by general formulae,
of the general formula (IId)

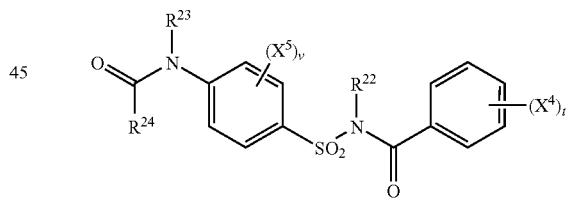

(IId)

or of the general formula (IIe)

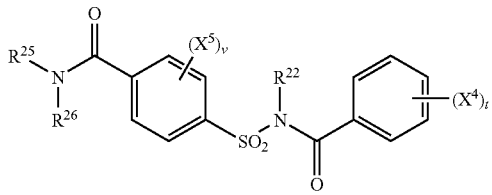

(IIe)

where
t represents a number 0, 1, 2, 3, 4 or 5,
v represents a number 0, 1, 2, 3, 4 or 5, $R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxyl-, halogen- or $C_1$-$C_4$-alkoxy-substituted $C_3$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl,
$X^4$ represents nitro, cyano, carboxyl, carbamoyl, formyl, sulfamoyl, hydroxyl, amino, halogen, $C_1$-$C_4$ alkyl, $C_1$-$C_4$-haloalkyl, $C_1$-$C_4$-alkoxy or $C_1$-$C_4$haloalkoxy, and
$X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$haloalkoxy.

The formula (I) provides a general definition of the compounds according to the invention. Preferred substituents or ranges of the radicals listed in the formulae given above and below are illustrated below:

A preferably represents hydrogen, represents $C_1$-$C_8$-alkyl, $C_2$-$C_8$-alkenyl, $C_2$-$C_8$-alkoxy-$C_1$-$C_4$-alkyl or $C_1$-$C_6$-alkylthio-$C_1$-$C_4$-alkyl, each of which is optionally mono- to trisubstituted by halogen, represents $C_3$-$C_8$-cycloalkyl which is optionally mono- to trisubstituted by halogen, $C_1$-$C_6$-alkyl or $C_1$-$C_6$-alkoxy, B preferably represents hydrogen, $C_1$-$C_6$-alkyl or $C_1$-$C_6$-alkoxy-$C_1$-$C_2$-alkyl or A, B and the carbon atom to which they are attached preferably represent saturated $C_3$-$C_8$-cycloalkyl or unsaturated $C_5$-$C_8$-cycloalkyl in which optionally one methylene group is replaced by oxygen or sulfur and which is optionally substituted by $C_1$-$C_6$-alkyl, $C_1$-$C_4$-haloalkyl or $C_1$-$C_6$-alkoxy, and D preferably represents hydrogen,
or
A preferably represents hydrogen or $C_1$-$C_8$-alkyl,
B preferably represents hydrogen and
D preferably represents $C_1$-$C_8$-alkyl, $C_1$-$C_8$-alkenyl, $C_1$-$C_6$-alkoxy-$C_2$-$C_4$-alkyl or $C_1$-$C_6$-alkylthio-$C_2$-$C_4$-alkyl, each of which is optionally mono- to pentasubstituted by halogen, represents $C_3$-$C_8$-cycloalkyl which is optionally mono- to trisubstituted by halogen, $C_1$-$C_4$-alkyl, $C_1$-$C_4$-alkoxy or $C_1$-$C_2$-haloalkyl, or A and D together preferably represent a $C_3$-$C_6$-alkanediyl or $C_3$-$C_6$-alkenediyl group in which in each case optionally one methylene group is replaced by oxygen or sulfur and which is in each case mono- to disubstituted by $C_1$-$C_4$-alkyl, $C_1$-$C_4$-alkoxy or $C_1$-$C_4$-haloalkyl or by a further $C_3$-$C_6$-alkanediyl, $C_3$-$C_6$-alkenediyl or $C_4$-$C_6$-alkanedienediyl group which forms a fused-on ring, G preferably represents one of the groups

(b)

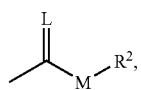
(c)

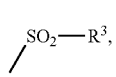
(d)

(e)

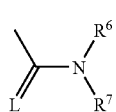
(f)

E or

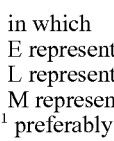
(g)

in which
E represents a metal ion equivalent or an ammonium ion,
L represents oxygen or sulfur and
M represents oxygen or sulfur,
$R^1$ preferably represents primary or secondary $C_1$-$C_{20}$-alkyl, $C_2$-$C_{20}$-alkenyl, $C_1$-$C_6$-alkoxy-$C_1$-$C_6$-alkyl, $C_1$-$C_6$-alkylthio-$C_1$-$C_6$-alkyl or poly-$C_1$-$C_4$-alkoxy-$C_1$-$C_4$-alkyl, each of which is optionally mono- to heptasubstituted by halogen, mono- to disubstituted by cyano, monosubstituted by $COR^{13}$, $C=N-OR^{13}$, $CO_2R^{13}$ or

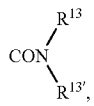

or represents $C_3$-$C_8$-cycloalkyl which is optionally mono- to trisubstituted by halogen, $C_1$-$C_4$-alkyl or $C_1$-$C_4$-alkoxy and in which optionally one or two not directly adjacent methylene groups are replaced by oxygen and/or sulfur,
represents phenyl, phenyl-$C_1$-$C_2$-alkyl or phenyl-$C_1$-$C_2$-alkenyl, each of which is optionally mono- to trisubstituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio, $C_1$-$C_6$-alkylsulfinyl or $C_1$-$C_6$-alkylsulfonyl,
represents 5- or 6-membered hetaryl which is optionally mono- to disubstituted by halogen or $C_1$-$C_6$-alkyl and which has one or two heteroatoms from the group consisting of oxygen, sulfur and nitrogen,
$R^2$ preferably represents $C_1$-$C_{20}$-alkyl, $C_2$-$C_{20}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by halogen,
represents $C_3$-$C_8$-cycloalkyl which is optionally mono- to disubstituted by halogen, $C_1$-$C_6$-alkyl or $C_1$-$C_6$-alkoxy or
represents phenyl or benzyl, each of which is optionally mono- to trisubstituted by halogen, cyano, nitro, $C_1$-$C_6$-alkyl, $C_1$-$C_6$-alkoxy, $C_1$-$C_6$-haloalkyl or $C_1$-$C_6$-haloalkoxy,
$R^3$ preferably represents $C_1$-$C_8$-alkyl which is optionally mono- to polysubstituted by halogen or represents phenyl or benzyl, each of which is optionally mono- to disubstituted by halogen, $C_1$-$C_6$-alkyl, $C_1$-$C_6$-alkoxy, $C_1$-$C_4$-haloalkyl, $C_1$-$C_4$-haloalkoxy, cyano or nitro, $R^4$ and $R^5$ independently of one another preferably represent $C_1$-$C_8$-alkyl, $C_1$-$C_8$-alkoxy, $C_1$-$C_8$-alkyl-amino, di($C_1$-$C_8$-alkyl)amino, $C_1$-$C_8$-alkylthio or $C_2$-$C_8$-alkenylthio, each of which is optionally mono- to trisubstituted by halogen, or represent phenyl, phenoxy or phenylthio, each of which is optionally mono- to trisubstituted by halogen, nitro, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl or $C_1$-$C_4$-haloalkyl, $R^6$ and $R^7$ independently of one another preferably represent hydrogen, represent $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, each of which is optionally mono- to trisubstituted by halogen, represent phenyl or benzyl, each of which is optionally mono- to trisubstituted by halogen, $C_1$-$C_8$-alkyl, $C_1$-$C_8$-haloalkyl or $C_1$-$C_8$-alkoxy, or together represent a $C_3$-$C_6$-alkylene radical which is optionally mono- to disubstituted by $C_1$-$C_4$-alkyl in which optionally one methylene group is replaced by oxygen or sulfur, $R^{13}$ preferably represents $C_1$-$C_6$-alkyl, $C_3$-$C_6$-alkenyl, $C_3$-$C_6$-alkynyl or $C_1$-$C_4$-alkoxy-$C_2$-$C_4$-alkyl, each of which is optionally mono- to trisubstituted by halogen, or represents $C_3$-$C_6$-cycloalkyl which is optionally mono- to disubstituted by halogen, $C_1$-$C_2$-alkyl or $C_1$-$C_2$-alkoxy and in which optionally one or two not directly adjacent methylene groups are replaced by oxygen or represents phenyl or phenyl-$C_1$-$C_2$-alkyl, each of which is optionally mono- to disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, $R^{13'}$ preferably represents hydrogen, $C_1$-$C_6$-alkyl or $C_3$-$C_6$-alkenyl.

In the radical definitions mentioned as being preferred, halogen represents fluorine, chlorine, bromine and iodine, in particular fluorine, chlorine and bromine.

A particularly preferably represents hydrogen, represents $C_1$-$C_6$-alkyl, $C_2$-$C_6$-alkenyl, $C_1$-$C_4$-alkoxy-$C_1$-$C_3$-alkyl or $C_1$-$C_4$-alkylthio-$C_1$-$C_3$-alkyl, each of which is optionally mono- to trisubstituted by fluorine or chlorine, or represents $C_3$-$C_6$-cycloalkyl which is optionally mono- to disubstituted by fluorine, chlorine, $C_1$-$C_2$-alkyl or $C_1$-$C_2$-alkoxy, B particularly preferably represents hydrogen, $C_1$-$C_4$-alkyl or $C_1$-$C_4$-alkoxy-$C_1$-$C_2$-alkyl,
or
A, B and the carbon atom to which they are attached particularly preferably represent saturated $C_3$-$C_7$-cycloalkyl in which optionally one methylene group is replaced by oxygen and which is optionally mono- to disubstituted by $C_1$-$C_4$-alkyl, $C_1$-$C_2$-haloalkyl or $C_1$-$C_4$-alkoxy, and D particularly preferably represents hydrogen,
or
A particularly preferably represents hydrogen or $C_1$-$C_6$-alkyl, B particularly preferably represents hydrogen and D particularly preferably represents $C_1$-$C_6$-alkyl, $C_3$-$C_6$-alkenyl, $C_1$-$C_4$-alkoxy-$C_2$-$C_3$-alkyl or $C_1$-$C_4$-alkylthio-$C_2$-$C_3$-alkyl, each of which is optionally mono- to trisubstituted by fluorine or chlorine, represents $C_3$-$C_6$-cycloalkyl which is optionally mono- to disubstituted by fluorine, chlorine, $C_1$-$C_2$-alkyl, $C_1$-$C_2$-alkoxy or trifluoromethyl, or A and D together particularly preferably represent a $C_3$-$C_5$-alkanediyl group in which optionally one methylene group is replaced by oxygen or sulfur and which is optionally mono- to disubstituted by $C_1$-$C_2$-alkyl, $C_1$-$C_2$-alkoxy or trifluoromethyl, or A and D together with the atoms to which they are attached represent one of the groups AD-1 to AD10

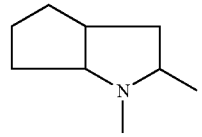

AD-1

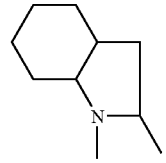

AD-2

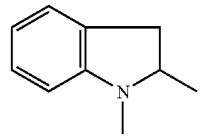

AD-3

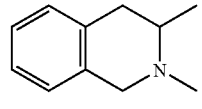

AD-4

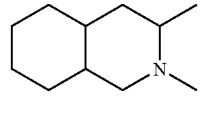

AD-5

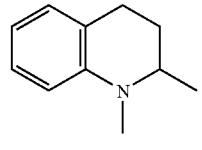

AD-6

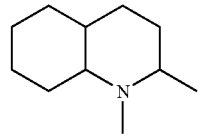

AD-7

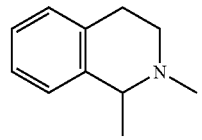

AD-8

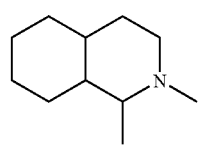

AD-9

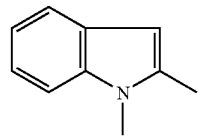

AD-10

G particularly preferably represents one of the groups

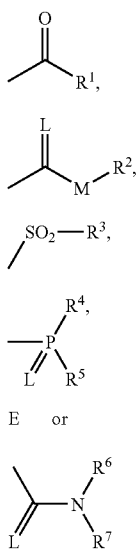

in which
E represents a metal ion equivalent or an ammonium ion,
L represents oxygen or sulfur and
M represents oxygen or sulfur, $R^1$ particularly preferably represents primary or secondary $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl or poly-$C_1$-$C_3$-alkoxy-$C_1$-$C_2$-alkyl, each of which is optionally mono- to pentasubstituted by fluorine or chlorine, monosubstituted by cyano or monosubstituted by CO—$R^{13}$, C=N—$OR^{13}$ or $CO_2R^{13}$, or represents $C_3$-$C_6$-cycloalkyl which is optionally mono- to disubstituted by fluorine, chlorine, $C_1$-$C_2$-alkyl or alkoxy and in which optionally one or two not directly adjacent methylene groups are replaced by oxygen,
represents phenyl or benzyl, each of which is optionally mono- to disubstituted by fluorine, chlorine, bromine, cyano, nitro, $C_1$-$C_4$-alkyl, $C_1$-$C_4$-alkylthio, $C_1$-$C_4$-alkylsulfinyl, $C_1$-$C_4$-alkylsulfonyl, $C_1$-$C_4$-alkoxy, $C_1$-$C_2$-haloalkyl or $C_1$-$C_2$-haloalkoxy,
represents pyrazolyl, thiazolyl, pyridyl, pyrimidyl, furanyl or thienyl, each of which is optionally mono- to disubstituted by fluorine, chlorine, bromine or $C_1$-$C_2$-alkyl, $R^2$ particularly preferably represents $C_1$-$C_{10}$-alkyl, $C_2$-$C_{10}$-alkenyl, $C_1$-$C_4$-alkoxy-$C_2$-$C_4$-alkyl or poly-$C_1$-$C_4$-alkoxy-$C_2$-$C_4$-alkyl, each of which is optionally mono- to trisubstituted by fluorine or chlorine,
represents $C_3$-$C_7$-cycloalkyl which is optionally monosubstituted by $C_1$-$C_2$-alkyl or $C_1$-$C_2$-alkoxy or
represents phenyl or benzyl, each of which is optionally mono- to disubstituted by fluorine, chlorine, bromine, cyano, nitro, $C_1$-$C_4$-alkyl, methoxy, trifluoromethyl or trifluoromethoxy, $R^3$ particularly preferably represents $C_1$-$C_4$-alkyl which is optionally mono- to trisubstituted by fluorine or chlorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ and $R^5$ independently of one another particularly preferably represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- to disubstituted by fluorine, chlorine, bromine, nitro, cyano, $C_1$-$C_3$-alkoxy, trifluoromethoxy, $C_1$-$C_3$-alkylthio, $C_1$-$C_3$-alkyl or trifluoromethyl, $R^6$ and $R^7$ independently of one another particularly preferably represent hydrogen, represent $C_1$-$C_6$-alkyl, $C_3$-$C_6$-cycloalkyl, $C_1$-$C_4$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl which is optionally mono- to disubstituted by fluorine, chlorine, bromine, trifluoromethyl, $C_1$-$C_4$-alkyl or $C_1$-$C_4$-alkoxy, or together represent a $C_5$-$C_6$-alkylene radical which is optionally mono- to disubstituted by methyl in which optionally one methylene group is replaced by oxygen, $R^{13}$ particularly preferably represents $C_1$-$C_4$-alkyl, $C_3$-$C_4$-alkenyl, $C_3$-$C_4$-alkynyl, or $C_1$-$C_4$-alkoxy-$C_2$-$C_3$-alkyl or represents $C_3$-$C_6$-cycloalkyl in each optionally one methylene group is replaced by oxygen.

In the radical definitions mentioned as being preferred, halogen represents fluorine, chlorine, bromine and iodine, in particular fluorine, chlorine and bromine.

A very particularly preferably represents hydrogen, methyl, ethyl, n-propyl, isopropyl, n-butyl, isobutyl, sec-butyl, tert-butyl, trifluoromethyl, methoxymethyl, ethoxymethyl, cyclopropyl, cyclopentyl or cyclohexyl, B very particularly preferably represents hydrogen, methyl or ethyl, or A, B and the carbon atom to which they are attached very particularly preferably represent saturated $C_6$-cycloalkyl in which optionally one methylene group is replaced by oxygen and which is optionally substituted by methyl, ethyl, trifluoromethyl, methoxy, ethoxy, n-propoxy, n-butyoxy or isobutoxy, and D very particularly preferably represents hydrogen,
or A very particularly preferably represents hydrogen, methyl or ethyl, B very particularly preferably represents hydrogen, and D very particularly preferably represents methyl, ethyl, n-propyl, isopropyl, n-butyl, sec-butyl, isobutyl, cyclopropyl, cyclopentyl or cyclohexyl, or A and D together very particularly preferably represent a $C_3$-$C_4$-alkanediyl group in which in each case optionally one methylene group is replaced by oxygen or sulfur and which is optionally mono- to disubstituted by methyl or methoxy, or A and D together with the atoms to which they are attached very particularly preferably represent the groups below:

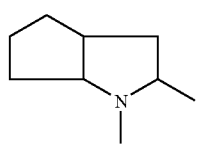

AD-1

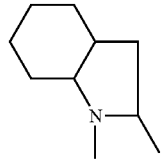

AD-2

G very particularly preferably represents one of the groups

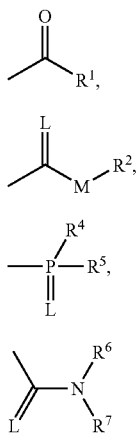

L represents oxygen and
M represents oxygen or sulfur,
R$^1$ very particularly preferably represents primary or secondary C$_1$-C$_6$-alkyl, C$_2$-C$_6$-alkenyl, C$_1$-C$_2$-alkoxy-C$_1$-C$_2$-alkyl, C$_1$-C$_2$-alkylthio-C$_1$-C$_2$-alkyl or poly-C$_1$-C$_2$-alkoxy-C$_1$-C$_2$-alkyl, each of which is optionally mono- to trisubstituted by fluorine or chlorine, or represents cyclopropyl, cyclopentyl or cyclohexyl, each of which is optionally monosubstituted by fluorine, chlorine, methyl, ethyl or methoxy,
represents phenyl which is optionally monosubstituted by fluorine, chlorine, bromine, cyano, nitro, methyl, ethyl, n-propyl, isopropyl, methoxy, ethoxy, methylthio, ethylthio, methylsulfinyl, ethylsulfinyl, methylsulfonyl, ethylsulfonyl, trifluoromethyl or trifluoro-methoxy,
represents furanyl, thienyl or pyridyl, each of which is optionally monosubstituted by chlorine, bromine or methyl,
R$^2$ very particularly preferably represents C$_1$-C$_8$-alkyl, C$_2$-C$_6$-alkenyl or C$_1$-C$_3$-alkoxy-C$_2$-C$_3$-alkyl, cyclopentyl or cyclohexyl,
or represents phenyl or benzyl, each of which is optionally monosubstituted by fluorine, chlorine, bromine, cyano, nitro, methyl, methoxy, trifluoromethyl or trifluoromethoxy,
R$^4$ very particularly preferably represents C$_1$-C$_6$-alkoxy,
R$^5$ very particularly preferably represents C$_1$-C$_6$-alkoxy,
R$^6$ very particularly preferably represents hydrogen, represents C$_1$-C$_4$-alkyl, C$_3$-C$_6$-cycloalkyl or allyl, represents phenyl which is in each case optionally monosubstituted by fluorine, chlorine, bromine, methyl, methoxy or trifluoromethyl,
R$^7$ very particularly preferably represents methyl, ethyl, n-propyl, isopropyl or allyl,
R$^6$ and R$^7$ together very particularly preferably represent a C$_5$-C$_6$-alkylene radical in which optionally one methylene group is replaced by oxygen.
A especially preferably represents methyl, ethyl or cyclopropyl,
B especially preferably represents methyl or ethyl,
A, B and the carbon atom to which they are attached especially preferably represent saturated C$_6$-cycloalkyl which is optionally substituted by methyl or methoxy,
D especially preferably represents hydrogen,
or
A especially preferably represents methyl or ethyl,
B especially preferably represents hydrogen, D especially preferably represents methyl, ethyl or cyclopropyl,
A and D together especially preferably represent a C$_3$-C$_4$-alkanediyl group which is optionally monosubstituted by methoxy,
A and D together with the atoms to which they are attached especially preferably represent the groups AD-1 and AD-2,
G especially preferably represents one of the groups

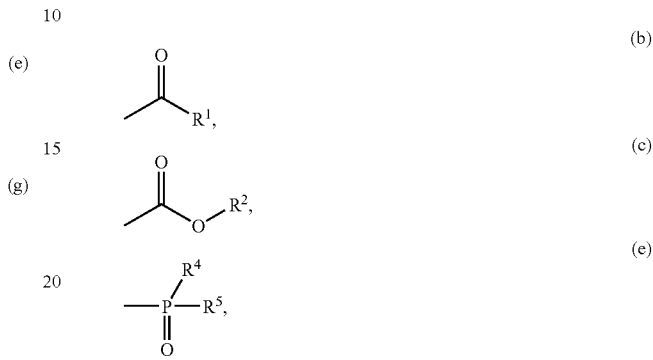

R$^1$ especially preferably represents primary or secondary C$_1$-C$_6$-alkyl, C$_2$-C$_6$-alkenyl, C$_1$-C$_2$-alkoxy-C$_1$-C$_2$-alkyl, C$_1$-C$_2$-alkylthio-C$_1$-C$_2$-alkyl or poly-C$_1$-C$_2$-alkoxy-C$_1$-C$_2$-alkyl, each of which is optionally mono- to trisubstituted by fluorine or chlorine, or represents cyclopropyl, cyclopentyl or cyclohexyl, each of which is optionally monosubstituted by fluorine, chlorine, methyl, ethyl or methoxy,
represents phenyl which is optionally monosubstituted by fluorine, chlorine, bromine, cyano, nitro, methyl, ethyl, n-propyl, isopropyl, methoxy, ethoxy, methylthio, ethylthio, methylsulfinyl, ethylsulfinyl, methylsulfonyl, ethylsulfonyl, trifluoromethyl or trifluoro-methoxy,
represents furanyl, thienyl or pyridyl, each of which is optionally monosubstituted by chlorine, bromine or methyl, (and represents in particular primary or secondary C$_1$-C$_6$-alkyl or C$_1$-C$_2$-alkoxy-C$_1$-C$_2$-alkyl),
R$^2$ especially preferably represents C$_1$-C$_8$-alkyl, C$_2$-C$_6$-alkenyl or C$_1$-C$_3$-alkoxy-C$_2$-C$_3$-alkyl, cyclopentyl or cyclohexyl,
or represents phenyl or benzyl, each of which is optionally monosubstituted by fluorine, chlorine, bromine, cyano, nitro, methyl, methoxy, trifluoromethyl or trifluoromethoxy, (and represents in particular C$_1$-C$_8$-alkyl or C$_2$-C$_6$-alkenyl),
R$^4$ especially preferably represents C$_1$-C$_6$alkoxy,
R$^5$ especially preferably represents C$_1$-C$_6$-alkoxy.

The general or preferred radical definitions or illustrations given above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings given above as being preferred (preferably).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Special preference according to the invention is given to the compounds of the formula (I) which contain a combination of the meanings given above as being especially preferred.

Saturated or unsaturated hydrocarbon radicals, such as alkyl, alkanediyl or alkenyl, can in each case be straight-chain or branched as far as this is possible, including in the combination with heteroatoms, such as, for example, in alkoxy.

Unless indicated otherwise, optionally substituted radicals can be mono- or polysubstituted, where in the case of polysubstitution the substituents can be identical or different.

In addition to the compounds mentioned in the preparation examples, particular mention may be made of the following compounds of the formulae (I-b) and (I-c):

TABLE 1

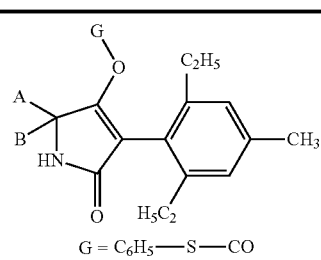

$G = C_6H_5-S-CO$

| A | B |
|---|---|
| $-(CH_2)_2-$ | |
| $-(CH_2)_4-$ | |
| $-(CH_2)_5-$ | |
| $-(CH_2)_6-$ | |
| $-(CH_2)_7-$ | |
| $-(CH_2)_2-O-(CH_2)_2-$ | |
| $-CH_2-O-(CH_2)_3-$ | |
| $-(CH_2)_2-S-(CH_2)_2-$ | |
| $-CH_2-CHCH_3-(CH_2)_3-$ | |
| $-(CH_2)_2-CHCH_3-(CH_2)_2-$ | |
| $-(CH_2)_2-CHOCH_3-(CH_2)_2-$ | |
| $-(CH_2)_2-CHOC_2H_5-(CH_2)_2-$ | |
| $-(CH_2)_2-CHOC_3H_7-(CH_2)_2-$ | |
| $-(CH_2)_2-CHO-C_4H_9-(CH_2)_2-$ | |
| $-(CH_2)_2-CH-O-i-C_4H_9-(CH_2)_2-$ | |
| $-(CH_2)_2-C(CH_3)_2-(CH_2)_2-$ | |
| $-CH_2-(CHCH_3)_2-(CH_2)_2-$ | |

A and B as defined in table 1,
Table 2 G=CH$_3$—CO
Table 3 G=C$_2$H$_5$—CO
Table 4 G=C$_3$H$_7$—CO
Table 5 G=i-C$_3$H$_7$—CO
Table 6 G=C$_4$H$_9$—CO
Table 7 G=i-C$_4$H$_9$—CO
Table 8 G=s-C$_4$H$_9$—CO
Table 9 G=t-C$_4$H$_9$—CO
Table 10

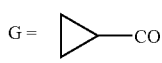

Table 11 G=H$_3$C—O—CH$_2$—CO
Table 12 G=H$_5$C$_2$—O—CH$_2$—CO
Table 13 G=H$_3$C—S—CH$_2$—CO
Table 14 G=H$_5$C$_2$—S—CH$_2$—CO
Table 15 G=CH$_3$—O—CO
Table 16 G=C$_2$H$_5$—O—CO
Table 17 G=C$_3$H$_7$—O—CO
Table 18 G=i-C$_3$H$_7$—O—CO
Table 19 G=C$_4$H$_9$—O—CO
Table 20 G=i-C$_4$H$_9$—O—CO
Table 21 G=s-C$_4$H$_9$—O—CO
Table 22 G=t-C$_4$H$_9$—O—CO
Table 23 G=t-C$_4$H$_9$—CH$_2$—O—CO
Table 24 G=C$_6$H$_5$—CH$_2$—O—CO
Table 25 G=C$_6$H$_5$—O—CO
Table 26 G=CH$_3$—S—CO
Table 27 G=C$_2$H$_5$—S—CO
Table 28 G=C$_3$H$_7$—S—CO
Table 29 G=i-C$_3$H$_7$—S—CO
Table 30 G=C$_4$H$_9$—S—CO
Table 31 G=i-C$_4$H$_9$—S—CO
Table 32 G=s-C$_4$H$_9$—S—CO
Table 33 G=t-C$_4$H$_9$—S—CO
Table 34 G=t-C$_4$H$_9$—CH$_2$—S—CO
Table 35 G=C$_6$H$_5$—CH$_2$—S—CO Preferred meanings of the cyclic ketoenols, mentioned above as active compounds in combination with the crop plant tolerance promoter compounds (herbicide safeners), of the formula (I-a) are defined below.

G preferably represents hydrogen,

A preferably represents hydrogen, $C_2$-$C_8$-alkyl, $C_1$-$C_4$-haloalkyl, represents $C_2$-$C_8$-alkenyl, $C_1$-$C_6$-alkoxy-$C_1$-$C_4$-alkyl or $C_1$-$C_6$-alkylthio-$C_1$-$C_4$-alkyl, each of which is optionally mono- to trisubstituted by halogen, represents $C_3$-$C_8$-cycloalkyl which is optionally mono- to trisubstituted by halogen, $C_1$-$C_6$-alkyl or $C_1$-$C_6$-alkoxy, B preferably represents hydrogen, $C_1$-$C_6$-alkyl or $C_1$-$C_6$-alkoxy-$C_1$-$C_2$-alkyl, or A, B and the carbon atom to which they are attached preferably represent $C_1$-$C_6$-alkyl-, $C_1$-$C_6$-alkoxy- or $C_1$-$C_4$-haloalkyl-substituted saturated $C_3$-$C_8$-cycloalkyl or represent unsaturated $C_5$-$C_8$-cycloalkyl or represent $C_5$-$C_8$-cycloalkyl in which one methylene group is replaced by oxygen or sulfur and which is optionally mono- to disubstituted by $C_1$-$C_6$-alkyl, D preferably represents hydrogen, or A preferably represents hydrogen or $C_1$-$C_8$-alkyl, B preferably represents hydrogen, D preferably represents $C_2$-$C_8$-alkyl, $C_1$-$C_8$-alkenyl, $C_1$-$C_6$-alkoxy-$C_2$-$C_4$-alkyl or $C_1$-$C_6$-alkylthio-$C_2$-$C_4$-alkyl, each of which is optionally mono- to pentasubstituted by halogen, represents $C_3$-$C_8$-cycloalkyl which is optionally mono- to trisubstituted by halogen, $C_1$-$C_4$-alkyl, $C_1$-$C_4$-alkoxy or $C_1$-$C_2$-haloalkyl.

A and D together preferably represent a $C_3$-$C_6$-alkanediyl group or $C_3$-$C_6$-alkenediyl group in which in each case optionally one methylene group is replaced by oxygen or sulfur and which are in each case optionally mono- to disubstituted by $C_1$-$C_4$-alkyl, $C_1$-$C_4$-alkoxy or $C_1$-$C_4$-haloalkyl or by a further $C_3$-$C_6$-alkanediyl, $C_3$-$C_6$-alkenediyl or $C_4$-$C_6$-alkanedienediyl group which forms a fused-on ring, G particularly preferably represents hydrogen, A particularly preferably represents hydrogen, $C_2$-$C_6$-alkyl, $C_1$-$C_4$-haloalkyl, represents $C_2$-$C_6$-alkenyl, $C_1$-$C_4$-alkoxy-$C_1$-$C_3$-alkyl or $C_1$-$C_4$-alkylthio-$C_1$-$C_3$-alkyl, each of which is optionally mono- to trisubstituted by fluorine or chlorine, or represents $C_3$-$C_6$-cycloalkyl which is optionally mono- to disubstituted by fluorine, chlorine, $C_1$-$C_2$-alkyl or $C_1$-$C_2$-alkoxy, B particularly preferably represents hydrogen, $C_1$-$C_4$-alkyl or $C_1$-$C_4$-alkoxy-$C_1$-$C_2$-alkyl, or A, B and the carbon atom to which they are attached particularly preferably represent saturated $C_3$-$C_7$-cycloalkyl which is substituted by $C_1$-$C_4$-alkyl, $C_1$-$C_4$-alkoxy or $C_1$-$C_2$-haloalkyl or represent unsaturated $C_5$-$C_6$-cycloalkyl or represent $C_5$-$C_8$-cycloalkyl in which one methylene group is replaced by oxygen or sulfur and which is optionally mono- to disubstituted by $C_1$-$C_4$-alkyl, D particularly preferably represents hydrogen, or A particularly preferably represents hydrogen or $C_1$-$C_6$-alkyl, B particularly preferably represents hydrogen, D particularly preferably represents $C_2$-$C_6$-alkyl, $C_3$-$C_6$-alkenyl, $C_1$-$C_4$-alkoxy-$C_2$-$C_3$-alkyl or $C_1$-$C_4$-alkylthio-$C_2$-$C_3$-alkyl, each of which is optionally mono- to trisubstituted by fluorine or chlorine, represents $C_3$-$C_6$-cycloalkyl which is optionally mono- to disubstituted by fluorine, chlorine, $C_1$-$C_2$-alkyl, $C_1$-$C_2$-alkoxy or trifluoromethyl, A and D together particularly preferably represent a $C_3$-$C_5$-alkanediyl group in which optionally one methylene group is replaced by oxygen or sulfur and which is optionally mono- to disubstituted by $C_1$-$C_2$-alkyl, $C_1$-$C_2$-alkoxy or trifluoromethyl, or A and D together with the atoms to which they are attached represent one of the groups AD-1 to AD-10

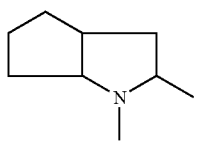

AD-1

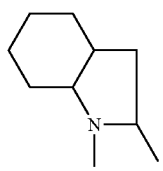

AD-2

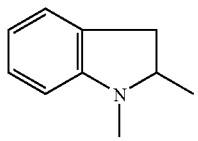

AD-3

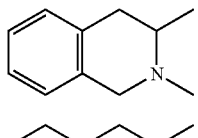

AD-4

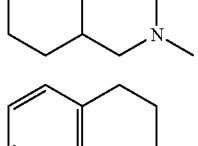

AD-5

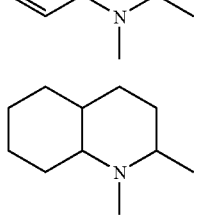

AD-6

AD-7

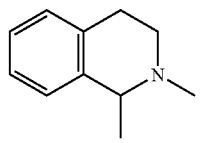

AD-8

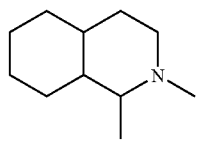

AD-9

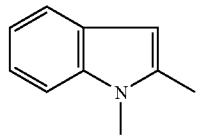

AD-10

G very particularly preferably represents hydrogen,

A very particularly preferably represents hydrogen, ethyl, n-propyl, isopropyl, n-butyl, isobutyl, sec-butyl, tert-butyl, trifluoromethyl, methoxymethyl, ethoxymethyl, cyclopropyl, cyclopentyl or cyclohexyl, B very particularly preferably represents hydrogen, methyl or ethyl, or A, B and the carbon atom to which they are attached very particularly preferably represent saturated $C_6$-cycloalkyl which is substituted by methyl, ethyl, trifluoromethyl, methoxy, ethoxy, n-propoxy, n-butoxy or isobutoxy or represent $C_6$-cycloalkyl in which one methylene group is replaced by oxygen and which is optionally monosubstituted by methyl or ethyl, D very particularly preferably represents hydrogen or A very particularly preferably represents hydrogen, methyl or ethyl, B very particularly preferably represents hydrogen, D very particularly preferably represents ethyl, n-propyl, isopropyl, n-butyl, sec-butyl, isobutyl, cyclopropyl, cyclopentyl or cyclohexyl, A and D together very particularly preferably represent a $C_3$-$C_4$-alkanediyl group in which in each case optionally one methylene group is replaced by oxygen or sulfur and which is optionally mono- to disubstituted by methyl or A and D together with the atoms to which they are attached represent the group below:

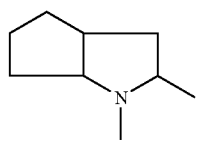

AD-1

Special preference is given to the compounds of the formula (I-a) listed in the table below:

(I-a)

| A | B | D |
|---|---|---|
| —(CH₂)₂—O—(CH₂)₂— | | H |
| —CH₂—O—(CH₂)₃— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHO—C₄H₉—(CH₂)₂— | | H |
| —(CH₂)₂—CH—O—i-C₄H₉—(CH₂)₂— | | H |
| —(CH₂)₂—C(CH₃)₂—(CH₂)₂— | | H |
| —CH₂—(CHCH₃)₂—(CH₂)₂— | | H |
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| cyclopropyl | CH₃ | H |
| cyclopentyl | CH₃ | H |
| cyclohexyl | CH₃ | H |

| A | D | B |
|---|---|---|
| H | C₂H₅ | H |
| H | C₃H₇ | H |
| H | i-C₃H₇ | H |
| H | C₄H₉ | H |
| H | i-C₄H₉ | H |
| CH₃ | C₂H₅ | H |
| C₂H₅ | C₂H₅ | H |
| H | cyclopropyl | H |
| H | cyclopentyl | H |
| H | cyclohexyl | H |
| —(CH₂)₃— | | H |
| —(CH₂)₄— | | H |
| —CH₂—S—(CH₂)₂— | | H |
| —CH₂—CH—CH— (with (CH₂)₃ bridge) | | H |

Preferred meanings of the groups listed above in connection with the crop plant tolerance promoter compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

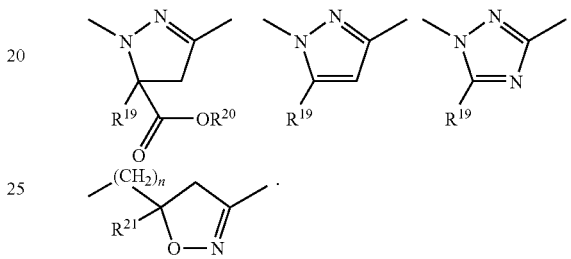

n preferably represents the numbers 0, 1, 2, 3 or 4.

$A^2$ preferably represents in each case optionally methyl-, ethyl-, methoxycarbonyl- or ethoxycarbonyl- or allyloxycarbonyl-substituted methylene or ethylene.

$R^{14}$ preferably represents hydroxyl, mercapto, amino, methoxy, ethoxy, n- or i-propoxy, n-, s- or t-butoxy, methylthio, ethylthio, n- or i-propylthio, n-, s- or t-butylthio, methylamino, ethylamino, n- or i-propylamino, n-, s- or t-butylamino, dimethylamino or diethylamino.

$R^{15}$ preferably represents hydroxyl, mercapto, amino, methoxy, ethoxy, n- or i-propoxy, n-, s- or t-butoxy, 1-methylhexyloxy, allyloxy, 1-allyloxymethylethoxy, methylthio, ethylthio, n- or i-propylthio, n-, s- or t-butylthio, methylamino, ethylamino, n- or i-propylamino, n-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl.

$R^{18}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl, or together with $R^{17}$ represents one of the radicals —CH₂—O—CH₂—CH₂— and —CH₂—CH₂—O—CH₂—CH₂— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

t preferably represents the numbers 0, 1, 2, 3 or 4, v preferably represents the numbers 0, 1, 2, or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, s- or t-butyl, methoxy, ethoxy, n- or i-propoxy, n-, s- or t-butoxy, methylthio, ethylthio, n- or i-propylthio, n-, s- or t-butylthio, methylamino, ethylamino, n- or i-propylamino, n-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulfamoyl, hydroxyl, amino, fluorine, chlorine, bromine, methyl, ethyl, n- or i-propyl, n-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulfamoyl, hydroxyl, amino, fluorine, chlorine, bromine, methyl, ethyl, n- or i-propyl, n-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

$(X^1)_m$—[phenyl with positions 2, 3, 4]—$A^1$—C(=O)—$R^{14}$

| Example No. | (Positions) $(X^1)_m$ | $A^1$ | $R^{14}$ |
|---|---|---|---|
| IIa-1 | (2) Cl, (4) Cl | [pyrazoline with $H_3C$ and $C(=O)OCH_3$] | $OCH_3$ |
| IIa-2 | (2) Cl, (4) Cl | [pyrazoline with $H_3C$ and $C(=O)OC_2H_5$] | $OCH_3$ |
| IIa-3 | (2) Cl, (4) Cl | [pyrazoline with $H_3C$ and $C(=O)OCH_3$] | $OC_2H_5$ |
| IIa-4 | (2) Cl, (4) Cl | [pyrazoline with $H_3C$ and $C(=O)OC_2H_5$] | $OC_2H_5$ |

TABLE-continued

Examples of the compounds of the formula (IIa)

(IIa)

$(X^1)_m$—(phenyl with positions 2,3,4)—$A^1$—C(=O)—$R^{14}$

| Example No. | (Positions) $(X^1)_m$ | $A^1$ | $R^{14}$ |
|---|---|---|---|
| IIa-5 | (2) Cl | 1-methyl-3-methyl-5-phenyl-pyrazole | OCH$_3$ |
| IIa-6 | (2) Cl, (4) Cl | 1-methyl-3-methyl-5-phenyl-pyrazole | OCH$_3$ |
| IIa-7 | (2) F | 1-methyl-3-methyl-5-phenyl-pyrazole | OCH$_3$ |
| IIa-8 | (2) F | 1-methyl-3-methyl-5-(2-chlorophenyl)-pyrazole | OCH$_3$ |
| IIa-9 | (2) Cl, (4) Cl | 1-methyl-3-methyl-5-trichloromethyl-1,2,4-triazole | OC$_2$H$_5$ |
| IIa-10 | (2) Cl, (4) CF$_3$ | 1-methyl-3-methyl-5-phenyl-1,2,4-triazole | OCH$_3$ |
| IIa-11 | (2) Cl | 1-methyl-3-methyl-5-(2-fluorophenyl)-pyrazole | OCH$_3$ |
| IIa-12 | — | 3-methyl-5-methyl-5-phenyl-4,5-dihydroisoxazole | OC$_2$H$_5$ |
| IIa-13 | (2) Cl, (4) Cl | 1-methyl-3-methyl-5-methyl-pyrazole | OC$_2$H$_5$ |
| IIa-14 | (2) Cl, (4) Cl | 1-methyl-3-methyl-5-isopropyl-pyrazole | OC$_2$H$_5$ |
| IIa-15 | (2) Cl, (4) Cl | 1-methyl-3-methyl-5-tert-butyl-pyrazole | OC$_2$H$_5$ |
| IIa-16 | (2) Cl, (4) Cl | 3-methyl-5-ethyl-4,5-dihydroisoxazole | OC$_2$H$_5$ |
| IIa-17 | (2) Cl, (4) Cl | 3,5-dimethyl-4,5-dihydroisoxazole | OC$_2$H$_5$ |
| IIa-18 | — | 3-methyl-5-methyl-5-phenyl-4,5-dihydroisoxazole | OH |

Examples of the compounds of the formula (IIb) which are very particularly preferred as herbicide safeners according to the invention are listed in the table below.

TABLE

Examples of the compounds of the formula (IIb)

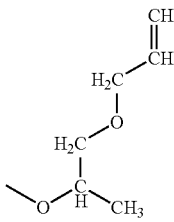

(IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH{=}CH_2$ |
| IIb-11 | (5) Cl | — | $CH_2$ | $OC_4H_9$-i |
| IIb-12 | (5) Cl | — | $CH_2$ | 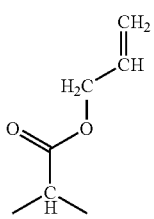 |
| IIb-13 | (5) Cl | — | 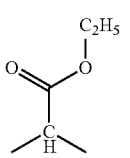 | $OCH_2CH{=}CH_2$ |
| IIb-14 | (5) Cl | — | 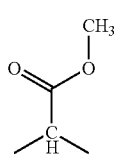 | $OC_2H_5$ |
| IIb-15 | (5) Cl | — |  | $OCH_3$ |

Examples of the compounds of the formula (IIc) which are very particularly preferred as herbicide safeners according to the invention are listed in the table below.

TABLE

Examples of the compounds of the formula (IIc)

(IIc)

$R^{16}-C(=O)-N(R^{17})(R^{18})$

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 2,2-dimethyl-3-methyl-oxazolidin-3-yl |
| IIc-3 | $CHCl_2$ | 2,2,5-trimethyl-3-methyl-oxazolidin-3-yl |
| IIc-4 | $CHCl_2$ | 3-methyl-1-oxa-3-azaspiro[4.5]decan-3-yl |
| IIc-5 | $CHCl_2$ | 2,2-dimethyl-3-methyl-5-phenyl-oxazolidin-3-yl |
| IIc-6 | $CHCl_2$ | 3,4-dimethyl-3,4-dihydro-2H-benzo[1,4]oxazin-4-yl |
| IIc-7 | $CHCl_2$ | 2,2-dimethyl-3-methyl-5-(furan-2-yl)-oxazolidin-3-yl |

Examples of the compounds of the formula (IId) which are very particularly preferred as herbicide safeners according to the invention are listed in the table below.

TABLE

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2-O-CH_3$ | (2) $OCH_3$ | — |

Examples of the compounds of the formula (IIe) which are very particularly preferred as herbicide safeners according to the invention are listed in the table below.

TABLE

Examples of the compounds of the formula (IIe)

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | CH$_3$ | (2) OCH$_3$ | — |
| IIe-2 | H | H | C$_2$H$_5$ | (2) OCH$_3$ | — |
| IIe-3 | H | H | C$_3$H$_7$-n | (2) OCH$_3$ | — |
| IIe-4 | H | H | C$_3$H$_7$-i | (2) OCH$_3$ | — |
| IIe-5 | H | H | cyclopropyl | (2) OCH$_3$ | — |
| IIe-6 | H | CH$_3$ | CH$_3$ | (2) OCH$_3$ | — |
| IIe-7 | H | H | CH$_3$ | (2) OCH$_3$ (5) CH$_3$ | — |
| IIe-8 | H | H | C$_2$H$_5$ | (2) OCH$_3$ (5) CH$_3$ | — |
| IIe-9 | H | H | C$_3$H$_7$-n | (2) OCH$_3$ (5) CH$_3$ | — |
| IIe-10 | H | H | C$_3$H$_7$-i | (2) OCH$_3$ (5) CH$_3$ | — |
| IIe-11 | H | H | cyclopropyl | (2) OCH$_3$ (5) CH$_3$ | — |
| IIe-12 | H | CH$_3$ | CH$_3$ | (2) OCH$_3$ (5) CH$_3$ | — |

Most preferred as crop plant tolerance promoter compound [component (c')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

Examples of the selective-herbicidal combinations according to the invention comprising in each case one active compound of the formula (I) and one of the safeners defined above are listed in the table below.

TABLE

Examples of the combinations according to the invention

| Active compounds of the formula (I) | Safeners |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

It has now surprisingly been found that the above-defined active-compound combinations of substituted ketoenols of the general formula (I) and (I-a) and safeners (antidotes) from the component (c') set out above combine very good useful plant tolerance with a high herbicidal activity and can be used in various crops, in particular in cereals (especially wheat), but also in soybeans, potatoes, maize and rice, for selective weed control.

In this context it is considered surprising that, from a multiplicity of known safeners or antidotes capable of antagonizing the damaging effect of a herbicide on the crop plants, it is specifically the compounds of component (c') set out above which are suitable for compensating—almost completely— the damaging effect of substituted cyclic ketoenols on the crop plants, without at the same time having any critical adverse effect on the herbicidal activity against the weeds.

Emphasis may be given here to the particularly advantageous effect of the particularly preferred and most preferred combination partners from component (c'), particularly with regard to the gentle treatment of cereal plants, such as wheat, barley and rye, for example, but also maize and rice, as crop plants.

Using, for example, according to process (Bα) 8-methyl-3-(2,6-diethyl-4-methylphenyl)-1-azaspiro[4,5]decane-2,4-dione and isobutyl chloride as starting materials, the course of the process according to the invention can be represented by the reaction scheme below:

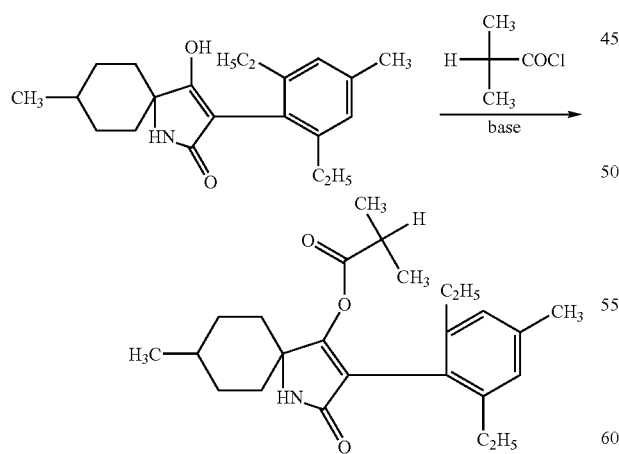

Using, for example, according to process (B) (variant β) 8-methoxy-3-(2,6-diethyl-4-methylphenyl)-1-azaspiro[4,5]decane-2,4-dione and acetic anhydride as starting materials, the course of the process according to the invention can be represented by the reaction scheme below:

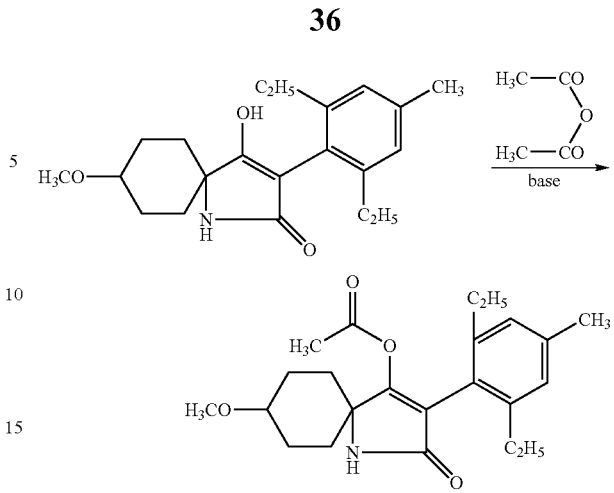

Using, for example, according to process (C) 8-methoxy 3-(2,6-diethyl-4-methylphenyl)-1-azaspiro[4,5]decane-2,4-dione and ethyl chloraformate as starting materials, the course of the process according to the invention can be represented by the reaction scheme below:

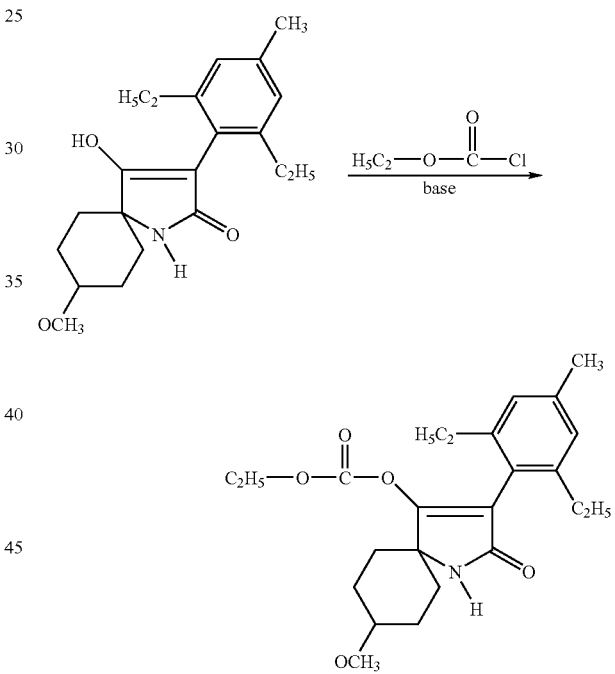

Using, for example, according to process (D), variant a 8-methyl 3-(2,6-diethyl-4-methylphenyl)-1-azaspiro[4,5]decane-2,4-dione and methyl chloromonothioformate as starting materials, the course of the reaction can be represented as follows:

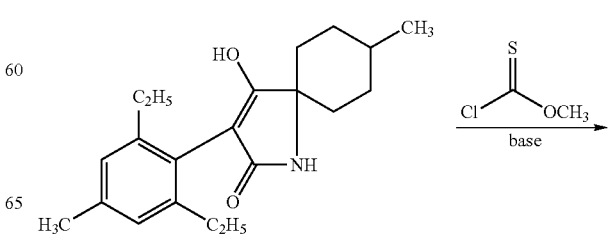

-continued

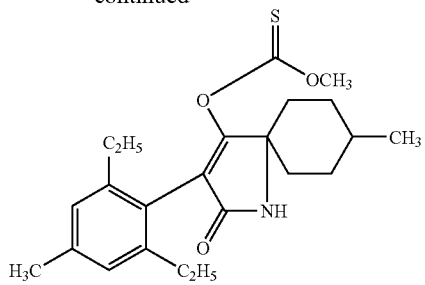

Using, for example, according to process (D), variant β 8-methoxy-3-(2,6-diethyl-4-methylphenyl)-1-azaspiro[4,5]decane-2,4-dione, carbon disulfide and methyl iodide as starting components, the course of the reaction can be represented as follows:

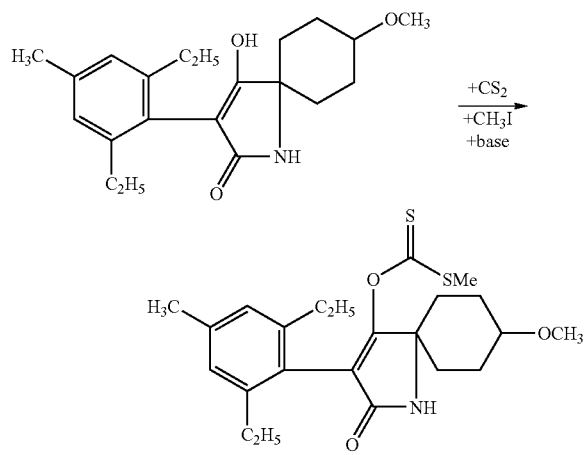

Using, for example, according to process (E) 8-methyl-3-(2,6-diethyl-4-methylphenyl)-1-azaspiro[4,5]decane-2,4-dione and methanesulfonyl chloride as starting material, the course of the reaction can be represented by the reaction scheme below:

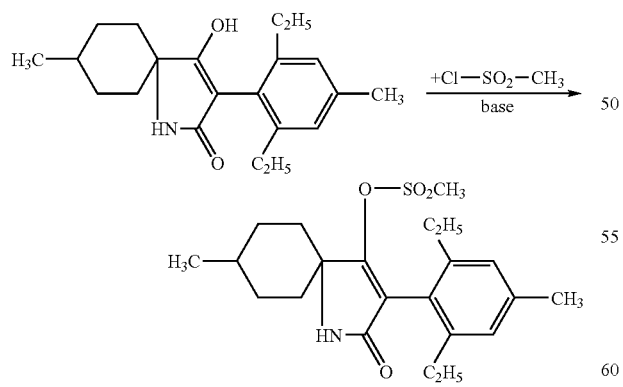

Using, for example, according to process (F) 8-methoxy 3-(2,6-diethyl-4-methylphenyl)-1-azaspiro[4,5]decane-2,4-dione and (2,2,2-trifluoroethyl)methanethiophosphonyl chloride as starting materials, the course of the reaction can be represented by the reaction scheme below:

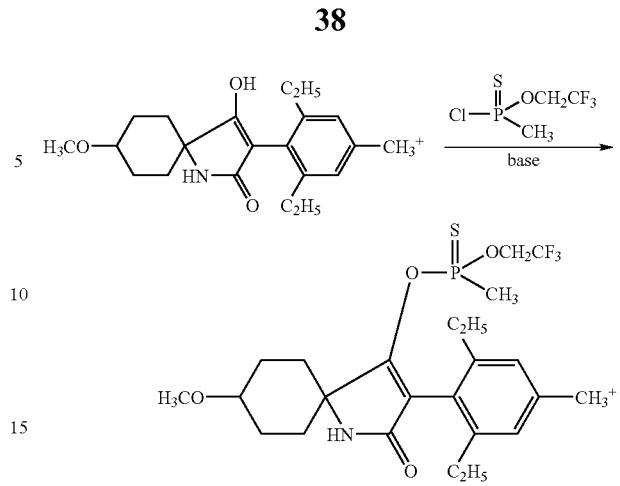

Using, for example, according to process (G) 8-methoxy-3-(2,6-diethyl-4-methylphenyl)-1-azaspiro[4,5]decane-2,4-dione and NaOH as components, the course of the process according to the invention can be represented by the reaction scheme below:

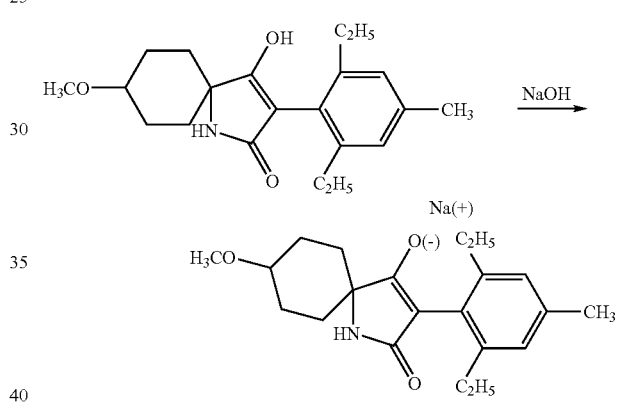

Using, for example, according to process (H) variant α 8-methoxy 3-(2,6-diethyl-4-methylphenyl)-1-azaspiro[4,5]decane-2,4-dione and ethyl isocyanate as starting materials, the course of the reaction can be represented by the reaction scheme below:

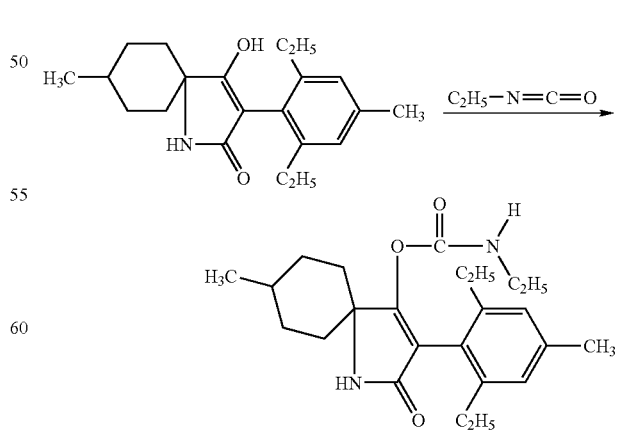

Using, for example, according to process (H) variant β 8-methoxy-3-(2,6-diethyl-4-methylphenyl)-1-azaspiro[4,5]

decane-2,4-dione and dimethylcarbamoyl chloride as starting materials, the course of the reaction can be represented by the scheme below:

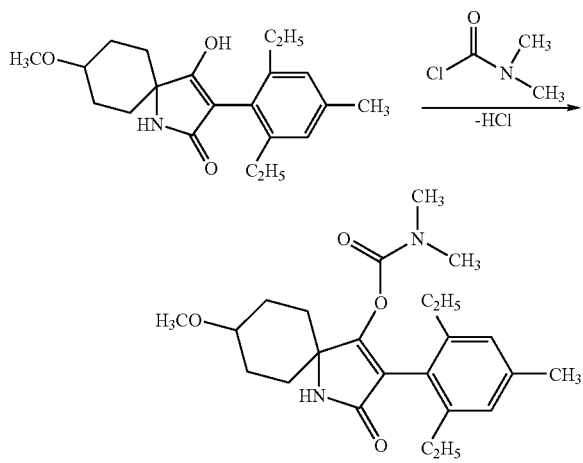

Some of the compounds, required as starting materials in the process (A) according to the invention, of the formula (Ia)

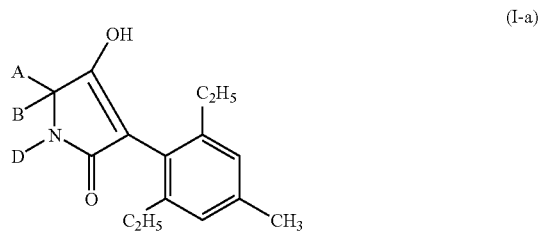

in which
A, B and D are as defined above
are novel (WO 01/17972, WO 01/74770) or they can be prepared by the processes described therein in principle.

The acid halides of the formula (II), carboxylic anhydrides of the formula (III), chloroformic esters or chloroformic thioesters of the formula (IV), chloromonothioformic esters or chlorodithioformic esters of the formula (V), alkyl halides of the formula (VI), sulfonyl chlorides of the formula (VII), phosphorus compounds of the formula (VIII) and metal hydroxides, metal alkoxides or amines of the formula (IX) and (X) and isocyanates of the formula (XI) and carbamoyl chlorides of the formula (XII) furthermore required as starting materials for carrying out the processes (A), (B), (C), (D), (E), (F) and (G) according to the invention are generally known compounds of organic or inorganic chemistry.

The process (Aα) is characterized in that compounds of the formula (I-a) are in each case reacted with carbonyl halides of the formula (II), if appropriate in the presence of a diluent and if appropriate in the presence of an acid binder.

Suitable diluents for use in the process (Aα) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane. The hydrolytic stability of the acid halide permitting, the reaction can also be carried out in the presence of water.

Suitable acid binders for the reaction according to process (Aα) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process (Aα) according to the invention may be varied within a relatively wide range. In general, the process is carried out at temperatures between −20° C. and +150° C., preferably between 0° C. and 100° C.

When carrying out the process (Aα) according to the invention, the starting materials of the formula (I-a) and the carbonyl halide of the formula (II) are generally each employed in approximately equivalent amounts. However, it is also possible to use a relatively large excess (up to 5 mol) of the carbonyl halide. Work-up is carried out by customary methods.

The process (Aβ) is characterized in that compounds of the formula (I-a) are in each case reacted with carboxylic anhydrides of the formula (III), if appropriate in the presence of a diluent and if appropriate in the presence of an acid binder.

Suitable diluents for use in the process (AβB according to the invention are, preferably, those diluents which are also preferred when acid halides are used. Besides, it is also possible for excess carboxylic anhydride to act simultaneously as diluent.

Suitable optional binders in the process (Aβ) are, preferably, those acid binders which are also preferred when acid halides are used.

The reaction temperature in the process (Aβ) according to the invention can be varied within a relatively wide range. In general, the process is carried out at temperatures between −20° C. and +150° C., preferably between 0° C. and 100° C.

When carrying out the process (Aβ) according to the invention, the starting materials of the formula (I-a) and the carboxylic anhydride of the formula (III) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and also the carboxylic acid formed are removed by distillation or by washing with an organic solvent or with water.

The process (B) is characterized in that compounds of the formula (I-a) are in each case reacted with chloroformic esters or chloroformic thioesters of the formula (IV), if appropriate in the presence of a diluent and if appropriate in the presence of an acid binder.

Suitable acid binders for the process (B) according to the invention are all customary acid acceptors.

Preference is given to using tertiary amines, such as triethylamine, pyridine, DABCO, DBU, DBA, Hünig base and N,N-dimethylaniline, furthermore, alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (B) according to the invention are all solvents which are inert to the chloroformic esters or chloroformic thioesters. Preference is given to using hydrocarbons, such as benzine, benzenes, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additional carboxylic esters, such as ethyl acetate, and also strongly polar solvents, such as dimethyl sulfoxide and sulfolane.

When carrying out the process (B) according to the invention, the reaction temperature may be varied within a relatively wide range. In general, the reaction temperature is between −20° C. and +100° C., preferably between 0° C. and 50° C.

The process (B) according to the invention is generally carried out under atmospheric pressure.

When carrying out the process (B) according to the invention, the starting materials of the formula (I-a) and the appropriate chloroformic ester or chloroformic thioester of the formula (IV) are generally each employed in approximately equivalent amounts. However, it is also possible to use a relatively large excess (up to 20 mol) of one component or the other. Work-up is carried out by customary methods. In general, precipitated salts are removed and the reaction mixture that remains is concentrated by removing the diluent under reduced pressure.

The process (C) according to the invention is characterized in that compounds of the formula (I-a) are in each case reacted with (Cα) compounds of the formula (V) in the presence of a diluent and, if appropriate, in the presence of an acid binder or (Cβ) carbon disulfide and subsequently with alkyl halides of the formula (VI), if appropriate in the presence of a diluent and if appropriate in the presence of a base.

In preparation process (Cα), about 1 mol of chloromonothioformic ester or chlorodithioformic ester of the formula (VI) is reacted per mole of the starting material of the formula (I-a), at from 0 to 120° C., preferably from 20 to 60° C.

Suitable diluents which are added, if appropriate, are all inert polar organic solvents, such as ethers, esters, amides, sulfones, sulfoxides, and also halogenated alkanes.

Preference is given to using dimethyl sulfoxide, ethyl acetate, tetrahydrofuran, dimethylformamide or methylene chloride.

If, in a preferred embodiment, the enolate salt of the compound (I-a) is prepared by adding strong deprotonating agents, such as, for example, sodium hydride or potassium tert-butoxide, the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

In preparation process (Cβ), in each case an aquimolar amount of in excess of carbon disulfide is added per mole of starting materials of the formula (I-a). Here, the process is preferably carried out at temperatures of from 0 to 50° C. and in particular at from 20 to 30° C.

Frequently, it is expedient to prepare initially the corresponding salt from the compounds of the formula (I-a) by adding a base (such as, for example, potassium tert-butoxide or sodium hydride). In each case, the compound (I-a) is reacted with carbon disulfide until the formation of the intermediate has ended, for example after stirring for a number of hours at room temperature.

Suitable bases for use in the process (Cβ) are all customary proton acceptors. Preference is given to using alkali metal hydrides, alkali metal alkoxides, alkali metal or alkaline earth metal carbonates or bicarbonates or nitrogen bases. Sodium hydride, sodium methoxide, sodium hydroxide, calcium hydroxide, potassium carbonate, sodium bicarbonate, triethylamine, dibenzylamine, diisopropylethylamine, pyridine, quinoline, diazabicyclooctane (DABCO), diazabicyclonone (DBN) and diazabicycloundecene (DBU) may be mentioned by way of example.

Suitable diluents for use in this process are all customary solvents.

Preference is given to using aromatic hydrocarbons, such as benzene or toluene, alcohols, such as methanol, ethanol, isopropanol or ethylene glycol, nitriles, such as acetonitrile, ethers, such as tetrahydrofuran and dioxane, amides, such as dimethylformamide, or other polar solvents, such as dimethyl sulfoxide or sulfonane.

The further reaction with the alkyl halide of the formula (VI) is preferably carried out at from 0 to 70° C. and in particular at from 20 to 50° C. Here, at least an aquimolar amount of alkyl halide is used.

The process is carried out at atmospheric pressure or under elevated pressure, preferably at atmospheric pressure.

Work-up is again carried out by customary methods.

The process (D) according to the invention is characterized in that compounds of the formula (I-a) are in each case reacted with sulfonyl chlorides of the formula (VII), if appropriate in the presence of a diluent and if appropriate in the presence of an acid binder.

In preparation process (D), about 1 mol of sulfonyl chloride of the formula (VII) is reacted per mole of starting material of the formula (I-a), at from −20 to 150° C., preferably from 20 to 70° C.

The process (D) is preferably carried out in the presence of a diluent.

Suitable diluents are all inert polar organic solvents, such as ethers, esters, amides, nitriles, sulfones, sulfoxides or halogenated hydrocarbons, such as methylene chloride.

Preference is given to using dimethyl sulfoxide, tetrahydrofuran, ethyl acetate, dimethylformamide, methylene chloride.

If, in a preferred embodiment, the enolate salt of the compound (I-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydride, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (E) according to the invention is characterized in that compounds of the formula (I-a) are in each case reacted with phosphorus compounds of the formula (VIII), if appropriate in the presence of a diluent and if appropriate in the presence of an acid binder.

In preparation process (E), to obtain compounds of the formula (I-e), from 1 to 2, preferably from 1 to 1.3 mol of the phosphorus compound of the formula (VIII) are reacted per mole of the compound (I-a), at temperatures between −40° C. and 150° C., preferably between −10 and 110° C.

The process (E) is preferably carried out in the presence of a diluent.

Suitable diluents are all inert polar organic solvents, such as ethers, esters, amides, nitriles, sulfides, sulfones, sulfoxides, etc.

Preference is given to using acetonitrile, ethyl acetate, dimethyl sulfoxide, tetrahydrofuran, dimethyl-formamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or by "insipient distillation", i.e. the removal of the volatile components under reduced pressure.

The process (F) is characterized in that compounds of the formula (I-a) are in each case reacted with metal hydroxides or metal alkoxides of the formula (IX) or amines of the formula (X), if appropriate in the presence of a diluent.

Suitable diluents for use in the process (F) according to the invention are, preferably, ethers, such as tetrahydrofuran, dioxane, diethyl ether, or else alcohols, such as methanol, ethanol, isopropanol, but also water. The process (F) according to the invention is generally carried out under atmospheric pressure. The reaction temperatures are generally between −20° C. and 100° C., preferably between 0° C. and 50° C.

The process (G) according to the invention is characterized in that compounds of the formula (I-a) are in each case reacted with (Gα) compounds of the formula (XI), if appropriate in the presence of a diluent and if appropriate in the presence of a catalyst, or (Gβ) with compounds of the formula (XII), if appropriate in the presence of a diluent and if appropriate in the presence of an acid binder.

In preparation process (Gα), about 1 mol of isocyanate of the formula (XI) is reacted per mole of starting material of the formula (I-a), at from 0 to 100° C., preferably from 20 to 50° C.

The process (Gα) is preferably carried out in the presence of a diluent.

Suitable diluents are all inert organic solvents, such as ethers, esters, amides, nitriles, sulfones or sulfoxides.

If appropriate, catalysts may be added to promote the reaction. Suitable for use as catalysts are, very advantageously, organotin compounds, such as, for example, dibutyltin dilaurate.

The process is preferably carried out at atmospheric pressure.

In preparation process (Gβ), about 1 mol of carbamoyl chloride of the formula (XII) is reacted per mole of starting material of the formula (I-a), at from 0 to 150° C., preferably from 20 to 70° C.

Suitable diluents which are added, if appropriate, are all inert polar organic solvents, such as ethers, esters, amides, sulfones, sulfoxides or halogenated hydrocarbons.

Preference is given to using dimethyl sulfoxide, ethyl acetate, tetrahydrofuran, dimethylformamide or methylene chloride.

If, in a preferred embodiment, the enolate salt of the compound (I-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out atmospheric pressure or under elevated pressure and is preferably carried out at atmospheric pressure. Work-up is carried out by customary methods.

The active compounds are well tolerated by plants, have favorable homeotherm toxicity and are environmentally friendly; they are suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp. and *Schistocerca gregaria*.

From the order of the Blattaria, for example, *Blatta orientalis*, *Periplaneta americana*, *Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp., *Damalinia* spp.

From the order of the Thysanoptera, for example, *Hercinothrips femoralis*, *Thrips tabaci*, *Thrips palmi*, *Frankliniella accidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Chematobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*,

*Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culexo* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example. *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds according to the invention may also be used in certain concentrations or application rates to act as herbicides and microbicides, for example as fungicides, antimycoties and bactericides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as mixing partners are, for example, the following:

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2 S)—N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:
1. Acetylcholine esterase (AChE) inhibitors
1.1 Carbamates, for Example
alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb
Triazamates
1.2 Organophosphates, for Example
acephate, azamethiphos, azinphos (-methyl, -ethyl), bromophos-ethyl, brom-fenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion
2. Sodium Channel Modulators/Voltage-Dependent Sodium Channel Blockers
2.1 Pyrethroids, for Example
acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
DDT
2.2 Oxadiazines, for Example Indoxacarb
3. Acetylcholine Receptor Agonists/Antagonists
3.1 Chloronicotinyls, for Example
  acetamiprid, clothianidin, dinotefuran, imidacloprid, nitenpyram, nithiazine, thiacloprid, thiamethoxam
3.2 Nicotine, Bensultap, Cartap
4. Acetylcholine Receptor Modulators
4.1 Spinosyns, for Example Spinosad
5. GABA-Controlled Chloride Channel Antagonists
5.1 Cyclodiene Organochlorines, for Example
  camphechlor, chlordane, endosulfan, gamma-HCH, HCH, heptachlor, lindane, methoxychlor
5.2 Fiproles, for Example
  acetoprole, ethiprole, fipronil, vaniliprole
6. Chloride Channel Activators
6.1 Mectins, for Example
  avermectin, emamectin, emamectin-benzoate, ivermectin, milbemycin
7. Juvenile Hormone Mimetics, for Example
  diofenolan, epofenonane, fenoxycarb, hydroprene, kinoprene, methoprene, pyriproxifen, triprene
8. Ecdyson Agonists/Disruptors
8.1 Diacylhydrazines, for Example
  chromafenozide, halofenozide, methoxyfenozide, tebufenozide
9. Chitin Biosynthesis Inhibitors
9.1 Benzoylureas, for Example
  bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
9.2 Buprofezin
9.3 Cyromazine
10. Oxidative Phosphorylation Inhibitors, ATP Disruptors
10.1 Diafenthiuron
10.2 Organotins, for Example Azocyclotin, Cyhexatin, Fenbutatin-Oxide
11. Oxidative Phosphorylation Decouplers Acting by Interrupting the H-Proton Gradient
11.1 Pyrroles, for Example Chlorfenapyr
11.2 Dinitrophenols, for Example Binapacyrl, Dinobuton, Dinocap, DNOC
12. Site-I Electron Transport Inhibitors
12.1 METIs, for Example Fenazaquin, Fenpyroximate, Pyrimidifen, Pyridaben, Tebufenpyrad, Tolfenpyrad
12.2 Hydramethylnon
12.3 Dicofol
13. Site-II Electron Transport Inhibitors
  Rotenone
14. Site-III Electron Transport Inhibitors
  Acequinocyl, fluacrypyrim
15. Microbial Disruptors of the Insect Gut Membrane
  *Bacillus thuringiensis* strains
16. Fat Synthesis Inhibitors
  Tetronic acids, for example
    spirodiclofen, spiromesifen
  Tetramic acids, for example
    spirotetramat
17. Carboxamides, for Example Flonicamid
18. Octopaminergic Agonists, for Example Amitraz
19. Inhibitors of Magnesium-Stimulated ATPase, for Example Propargite
20. BDCAs, for example N2-[1,1-dimethyl-2-(methylsulfonyl)ethyl]-3-iodo-N-1-[2-methyl-4-[1,2,2,2-tetrafluoro-1-(trifluoromethyl)ethyl]phenyl]-1,2-benzenedicarboxamide (CAS-Reg.-No.: 272451-65-7)
21. Nereistoxin Analogs, for Example Thiocyclam Hydrogen Oxalate, Thiosultap-Sodium
22. Biologicals, Hormones or Pheromones, for Example azadirachtin, *Bacillus* spec., *Beauveria* spec., codlemone, *Metarrhizium* spec., *Paecilomyces* spec., thuringiensin, *Verticillium* spec.
23. Active Compounds with Unknown or Unspecific Mechanisms of Action
23.1 Fumigants, for Example
  aluminum phosphide, methyl bromide, sulfuryl fluoride
23.2 Selective Antifeedants, for Example
  cryolite, flonicamid, pymetrozine
23.3 Mite Growth Inhibitors, for Example
  clofentezine, etoxazole, hexythiazox
23.4 Amidoflumet, benclothiaz, benzoximate, bifenazate, bromopropylate, buprofezin, quino-methionate, chlordimeform, chlorobenzilate, chloropicrin, clothiazoben, cycloprene, di-cyclanil, fenoxacrim, fentrifanil, flubenzimine, flufenerim, flutenzin, gossyplure, hydra-methylnone, japonilure, metoxadiazone, petroleum, piperonyl butoxide, potassium oleate, pyridalyl, sulfluramid, tetradifon, tetrasul, triarathene, verbutin,
and also products which comprise insecticidal plant extracts, nematodes, fungi or viruses.

A mixture with other known active compounds, such as herbicides, or with fertilizers and growth regulators, safeners and/or semiochemicals is also possible.

When used as insecticides in their commercially available formulations and in the use forms prepared with these formulations, the active compounds according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared with these formulations, the active compounds according to the invention can furthermore be present in the form of a mixture with inhibitors which reduce the degradation of the active compound after application in the habitat of the plant, on the surface of parts of plants or in plant tissues.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound is distinguished by excellent residual action on wood and clay as well as good stability to alkali on limed substrates.

As already mentioned above, it is possible to treat all plants and their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetic modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes and slugs and snails, owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato).

Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the sub-class of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds according to the invention have a potent insecticidal action against insects which destroy industrial materials.

The following insects may be mentioned by way of example and as being preferred, but without any limitation:

Beetles, such as
*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus*.

Dermapterans, such as
*Sirex juvencus, Urocerus gigas, Urocerus gigas taignus, Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or allylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odor-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulfonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin,
and fungicides, such as epoxyconazole, hexaconazole, azaconazole, propiconazole, tebuconazole, cyproconazole, metconazole, imazalil, dichlorfluanid, tolylfluanid, 3-iodo-2-propynylbutyl carbamate, N-octyl-isothiazolin-3-one and 4,5-dichloro-N-octylisothiazolin-3-one.

The compounds according to the invention can at the same time be employed for protecting objects which come into contact with salt water or brackish water, in particular hulls, screens, nets, buildings, moorings and signaling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulfides, tri-n-butyltin laurate, tri-n-butyltin chloride, copper(I) oxide, triethyltin chloride, tri-n-butyl-(2-phenyl-4-chlorophenoxy)tin, tributyltin oxide, molybdenum disulfide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butyl-carbamate, tolylfluanid and azoles such as
azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb; Fe chelates;
or conventional antifouling active compounds such as
4,5-dichloro-2-octyl-4-isothiazolin-3-one, diiodomethylparatryl sulfone, 2-(N,N-dimethyl-thiocarbamoylthio)-5-nitrothiazyl, potassium, copper, sodium and zinc salts of 2-pyridinethiol 1-oxide, pyridine/triphenylborane, tetrabutyldistannoxane, 2,3,5,6-tetrachloro-4-(methylsulfonyl)-pyridine, 2,4,5,6-tetrachloroisophthalonitrile, tetramethylthiuram disulfide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used, for example, in the following plants:
Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibis-* cus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds. The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic colorants, such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are Suitable for the Mixtures are Known Herbicides, for Example
acetochlor, acifluorfen (-sodium), aclonifen, alachlor, alloxydim (-sodium), ametryne, amicarb-azone, amidochlor, amidosulfuron, aminopyralid, anilofos, asulam, atrazine, azafenidin, azimsulfuron, beflubutamid, benazolin (-ethyl), bencarbazone, benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flucetosulfuron, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), pyrimisulfan, quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazone-methyl, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron, triflosulam,

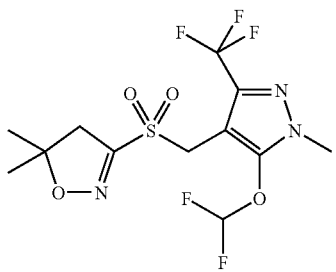

KIH 485

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, salts from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form in of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soybeans, potatoes, cotton, oilseed rape, beet, sugar cane and also fruit plants (with the fruits apples, pears, citrus fruits and grapevines), greater emphasis being given to maize, soybeans, potatoes, cotton and oilseed rape.

The term "active compounds" always also includes the active compound combinations mentioned here.

Preparation and use of the active compounds according to the invention is illustrated by the examples below.

Compounds of the formula (I-a) known from WO 01/74 770

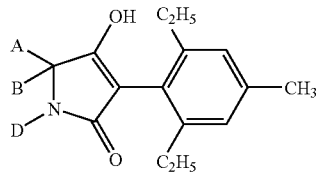

(I-a)

| Ex. No. | D | A | B | m.p. | Isomer |
|---|---|---|---|---|---|
| I-a-1 | H | —(CH$_2$)$_2$—CHOCH$_3$—(CH$_2$)$_2$— | | 244 | β |
| I-a-2 | H | —(CH$_2$)$_2$—CHOC$_2$H$_5$—(CH$_2$)$_2$— | | 212 | β |
| I-a-3 | H | ▷— | CH$_3$ | 227-229 | — |
| I-a-4 | H | C$_2$H$_5$ | CH$_3$ | 229-230 | — |
| I-a-5 | CH$_3$ | C$_2$H$_5$ | H | 220-224 | — |
| I-a-6 | ▷— | | CH$_3$ | H | 211-213 | — |
| I-a-7 | | —(CH$_2$)$_3$— | H | 195-198 | — |
| I-a-8 | | —CH$_2$—CHOCH$_3$—CH$_2$— | H | 233 | — |
| I-a-9 | | —CH—CH—CH$_2$— / (CH$_2$)$_4$ | H | *4.29 (dd, 1H, C$_5$—H)— 6.84 (s, 2H, Ar—H) | — |
| I-a-10 | H | —(CH$_2$)$_2$—CHCH$_3$—(CH$_2$)$_2$— | | *0.91 (d, 3H, CH$_3$-β) Spiral cycle 6.84 (s, 2H, Ar—H) | β |
| I-a-11 | H | —(CH$_2$)$_2$—CHCF$_3$—(CH$_2$)$_2$— | | Oil log P 3.05 | β |

*$^1$H-MNR (400 MHz, d$_6$-DMSO): shifts δ in ppm

PREPARATION EXAMPLES

Example I-b-1

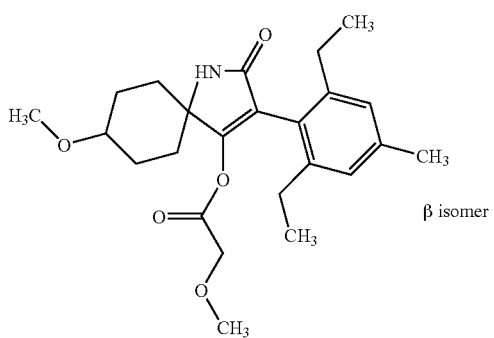

β isomer

Under reflux, 0.052 g (0.48 mmol) of methoxyacetal chloride in 2 ml of ethyl acetate is added to 0.15 g (0.437 mmol) of the compound of preparation example I-a-1 and 0.049 g (0.48 mmol) of triethylamine and 10 ml of ethyl acetate. The mixture is stirred under reflux for 20 h, and the reaction is monitored by thin-layer chromatography. After the reaction has ended, 2 ml of saturated NaHO$_3$ solution are added, and the mixture is stirred at room temperature for 10 min.

The organic phase is separated off, the solvent is removed using a rotary evaporator and the precipitate is saturated with n-heptane. The precipitate is filtered off with suction.

Yield: 0.137 g (76% of theory)

$^1$H-NMR (300 MHz, CDCl$_3$): δ 6.89 (s, 2H, Ar—H), 3.96 (s, 2H, CH$_2$OCH$_3$), 3.22 (m, 1H, CH—OCH$_3$) ppm.

Analogously to example (I-b-1) and in accordance with the general statements on the preparation, the following compounds of the formula (I-b) are obtained

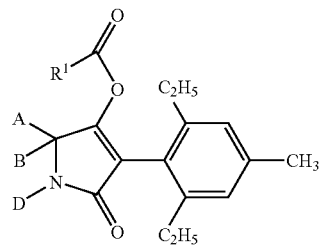

(I-b)

| Ex. No. | D | A | B | R¹ | m.p. ° C. | Isomer |
|---|---|---|---|---|---|---|
| I-b-2 | H | —(CH$_2$)$_2$—CHOCH$_3$—(CH$_2$)$_2$— | | H$_5$C$_2$—O—CH$_2$— | 138-141 | β |
| I-b-3 | H | —(CH$_2$)$_2$—CHOCH$_3$—(CH$_2$)$_2$— | | i-C$_3$H$_7$ | 182-185 | β |
| I-b-4 | H | △ | CH$_3$ | i-C$_3$H$_7$ | 128-129 | — |
| I-b-5 | H | C$_2$H$_5$ | CH$_3$ | i-C$_3$H$_7$ | 120 | — |
| I-b-6 | H | CH$_3$ | CH$_3$ | i-C$_3$H$_7$ | 166-168 | — |
| I-b-7 | H | △ | CH$_3$ | H$_5$C$_2$—O—CH$_2$— | 115 | — |
| I-b-8 | H | CH$_3$ | CH$_3$ | H$_3$C—O—CH$_2$— | *3.97 (s, 2H, C$\underline{H_2}$—O) 6.89 (s, 2H, Ar—H) | |
| I-b-9 | H | —(CH$_2$)$_2$—CHCH$_3$—(CH$_2$)$_2$— | | H$_3$C—O—CH$_2$— | *3.94 (s, 2H, C$\underline{H_2}$—O) 6.89 (s, 2H, Ar—H) | β |
| I-b-10 | —CH$_2$—CHOCH$_3$—CH$_2$— | | H | i-C$_3$H$_7$ | *3.37 (s, 3H, O—C$\underline{H_3}$) 6.89 (s, 2H, Ar—H) | — |
| I-b-11 | CH$_3$ | C$_2$H$_5$ | H | i-C$_3$H$_7$ | *3.03 (s, 3H, N—C$\underline{H_3}$) 6.89 (s, 2H, Ar—H) | — |
| I-b-12 | ▷ | CH$_3$ | H | i-C$_3$H$_7$ | *0.76 (m, 2H, CH$_2$— cyclopropyl), 6.88 (d, 2H, Ar—$\underline{H}$) | — |
| I-b-13 | | —(CH$_2$)$_3$— | | i-C$_3$H$_7$ | *4.71 (dd, 1H, C5—$\underline{H}$) 6.89 (d, 2H, Ar—$\underline{H}$) | — |
| I-b-14 | | —CH—CH—CH$_2$— (CH$_2$)$_4$ | | i-C$_3$H$_7$ | *2.58 (m, 1H, C$\underline{H}$(CH$_3$)$_2$— 4.97 (dd, 1H, C5—$\underline{H}$) 6.92 (s, 2H, Ar—H) | — |
| I-b-15 | H | —(CH$_2$)$_2$—CHCH$_3$—(CH$_2$)$_2$— | | i-C$_3$H$_7$ | *¹⁾0.96 (d, 6H, CH(C$\underline{H_3}$)$_2$) 2.29 (s, 3H, Ar—C$\underline{H_3}$) | β |

*¹H-NMR (300 MHz, CDCl$_3$): shifts δ in ppm
*¹⁾measured in CD$_3$OD

Example I-c-1

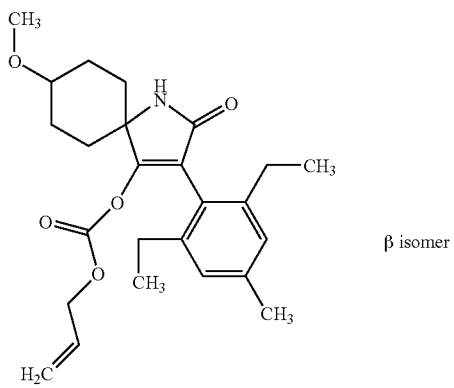 [SMILES: C=CCOC(=O)OC1=C(c2c(CC)cc(C)cc2CC)C(=O)NC12CCC(OC)CC2]

β isomer 0.21 g (0.6 mmol) of the compound of preparation example (I-a-1) was suspended in 10 ml of dichloromethane, and 0.1 ml of triethylamine and 0.08 g (0.66 mmol) of allyl chloroformate were then added at room temperature. The mixture was stirred over the weekend, and 10 ml of 5% strength sodium carbonate solution was added. After 4 h of stirring, the organic phase was separated off and concentrated to dryness. The residue obtained in this manner was taken up in 1 ml of ethyl acetate, and 2 ml of n-heptane were added. The solid is filtered off with suction.

Yield: 84 mg (32.7% of theory) m.p.: 155-157° C.

Analogously to example (I-c-1) and in accordance with the general statements on the preparation, the following compounds of the formula (I-c) are obtained

Example I-e-1

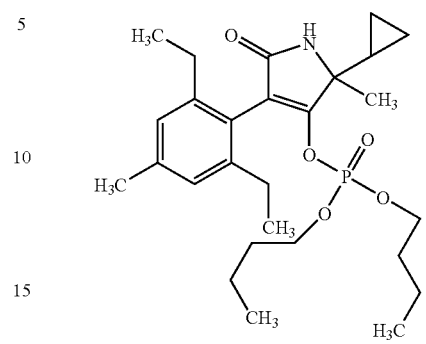

0.15 g (0.5 mmol) of the compound of example 1-a-3 is initially charged in acetonitrile (10 ml), and 0.083 g of potassium carbonate (1.2 eq) is added. After 30 min, dibutylphosphoryl chloride (0.126 g, 1.1 eq) is added, and the mixture is stirred at TR for 48 h. The solid is filtered with suction and the organic solution is concentrated and purified by chromatography (n-heptane/ethyl acetate 9:1 to 1:4). This gives 82 mg of a colorless oil (yield 32% of theory).

*$^1$H-NMR (300 MHz, CDCl$_3$): δ=0.21 (m, 2H, CH$_2$ from CycPr), 6.92 (d, 2H, Ar—H)

The compounds of the formula (I-a) can be prepared by the processes described in WO 01/74770:

(I-c)

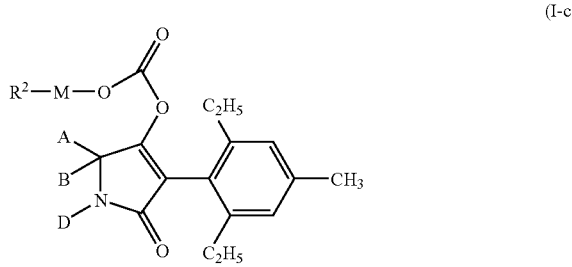

| Ex. No. | D | A | B | M | R² | m. p. ° C. | Isomer |
|---------|-----|------------------------------|-----|---|-------|----------------------------------|--------|
| I-c-2 | H | —(CH$_2$)$_2$—CHOCH$_3$—(CH$_2$)$_2$— | | O | C$_2$H$_5$ | 149 | β |
| I-c-3 | H | CH$_3$ | CH$_3$ | O | C$_2$H$_5$ | 182-184 | — |
| I-c-4 | CH$_3$ | C$_2$H$_5$ | H | O | C$_2$H$_5$ | *3.03 (s, 3H, NC$\underline{H}_3$) | — |
| | | | | | | 4.18 (m, 2H, C$\underline{H}_2$—O) | |
| | | | | | | 6.92 (s, 2H, Ar—H) | |
| I-c-5 | C$_2$H$_5$ | CH$_3$ | H | O | C$_2$H$_5$ | *1.47 (d, 3H, CHC$\underline{H}_3$) | — |
| | | | | | | 4.18 (m, 2H, C$\underline{H}_2$—O) | |
| | | | | | | 6.91 (s, 2H, Ar—$\underline{H}$) | |
| I-c-6 | | —(CH$_2$)$_3$— | H | O | C$_2$H$_5$ | *4.18 (m, 2H, C$\underline{H}_2$—O) | — |
| | | | | | | 4.74 (dd, 1H, C5—$\underline{H}$) | |
| | | | | | | 6.92 (d, 2H, Ar—$\underline{H}$) | |
| I-c-7 | | —CH$_2$—CHOCH$_3$—CH$_2$— | H | O | C$_2$H$_5$ | *3.36 (s, 3H, OC$\underline{H}_3$) | — |
| | | | | | | 4.18 (m, 2H, C$\underline{H}_2$—O) | |
| | | | | | | 6.92 (d, 2H, Ar—$\underline{H}$) | |

*$^1$H-NMR (300 MHz, CDCl$_3$): shifts δ in ppm

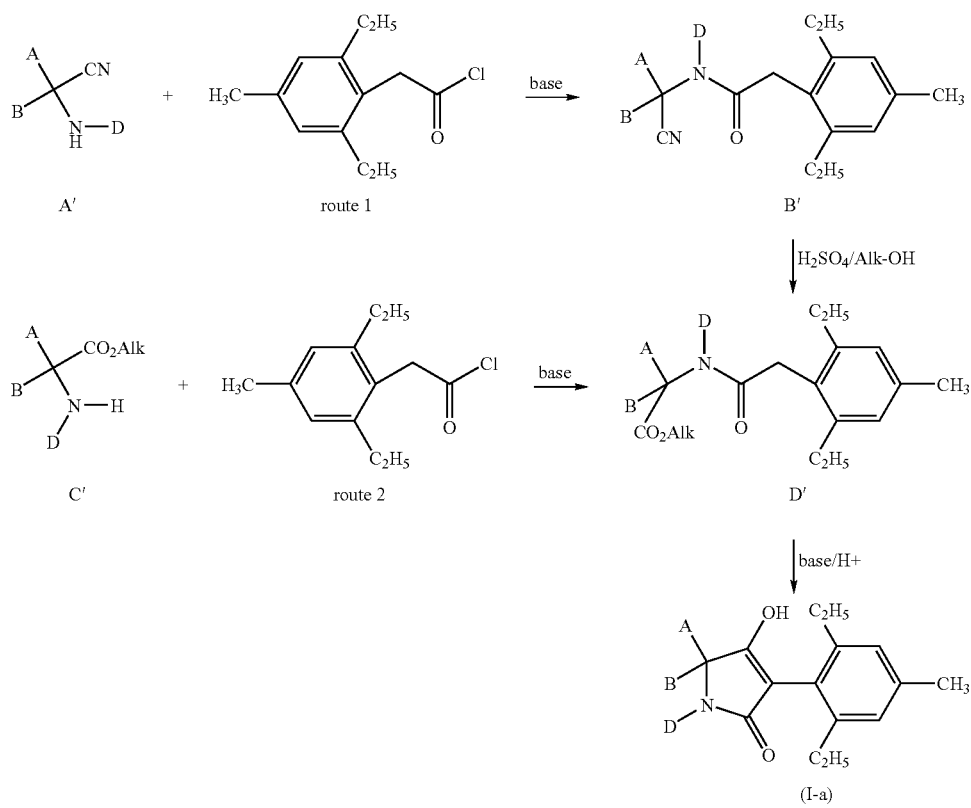

Here, the substituents A, B and D are as defined above and Alk represents $C_1$-$C_8$-alkyl, preferably methyl or ethyl.

Analogously to G. C. Lloyd-Jones, Angew. Chem. Int. Ed. 2002, 41, 953-956; S. L. Buchwald, W. A. Moradi, JACS 2001, 123, 7996-8002 and S. Lee, N. A. Beare, J. F. Hartwig JACS 2001, 123, 8410-8411, an improved process for preparing 2,6-diethyl-4-methylphenyl acetic acid was found.

The process is characterized in that 2,6-diethyl-4-methyl-bromobenzene is reacted with tert-butyl acetate, if appropriate in the presence of a diluent, if appropriate in the presence of a base, if appropriate in the presence of a phosphine ligand and if appropriate in the presence of palladium (0) compounds, and then reacted with an acid.

Suitable diluents for use in the process according to the invention are all solvents which are inert to the reagents. Preference is given to using hydrocarbons, such as benzine, benzene, toluene, xylene and tetraline, furthermore ethers, such as diethyl ether, dimethoxyethane, tetrahydrofuran and dioxane.

Suitable bases for the reaction according to the process according to the invention are lithium amide bases, preferably lithium hexyldisilazide, lithium diisopropylamide, lithium dicyclohexylamide.

Suitable phosphine ligands are, for example, in particular tri-tert-butylphosphine and 2-dicyclohexylphosphino (2'-N,N-dimethylamino)biphenyl.

A palladium (0) compound which may be mentioned by way of example is bis-(dibenzylideneacetone)-palladium.

Acids which may be mentioned are organic acids, for example formic acid, or inorganic acids, for example hydrochloric acid or sulfuric acid.

The reaction temperature in the process according to the invention may be varied within a relatively wide range. In general, the process is carried out at temperatures between −80° C. and +150° C., preferably between 0° C. and 100° C.

When carrying out the process according to the invention, the starting materials are generally each employed in approximately equivalent amounts.

A further process for preparing 2,6-diethyl-4-methylphenylacetic acid comprises the reaction of 2,6-diethyl-4-methylphenylmalodinitrile with acids, if appropriate in the presence of a diluent, and the subsequent reaction with an acid.

Suitable acids are mineral acids, for example concentrated sulfuric acid.

The reaction temperature may be varied within a relatively wide range. In general, the process is carried out at temperatures between 0 and 150° C. The starting materials are generally each employed in approximately equivalent amounts.

By reacting 2,6-diethyl-4-methylphenylacetic acid with halogenating agents, if appropriate in the presence of a diluent, 2,6-diethyl-4-methylphenylacetyl chloride is obtained (WO 01/74770).

Component D'
Route 1

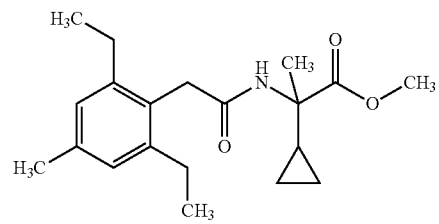

3.6 g (7.5 mmol) of component B' and 30 ml of dichloromethane are added dropwise to 2.32 ml of sulfuric acid. The mixture is stirred at 35° C. for 2 hours, and 3,25 ml of methanol are added. The mixture is stirred at 60° C. for 6 hours and left at room temperature overnight. The reaction mixture is poured into water and extracted with dichloromethane. The solvent is distilled off and the residue is taken up in ethyl acetate/n-heptane 1:4. The residue is filtered off with suction through a frit, washed with ethyl acetate/n-heptane 1:4, dried (0.5 g), and the solvent is removed using a rotary evaporator. The residue of the mother liquor is purified by column-chromatographic separation (silica gel, ethyl acetate/n-heptane 1:4→1:1. The fractions are concentrated using a concentrated evaporator, stirred with ethyl acetate/n-heptane 1:9 for 10 minutes and filtered off with suction through a frit, and the filter cake is washed with n-heptane and dried (0.85 g).

Total yield: 1.35 g (52% of theory), m.p. 95° C.

Component B'

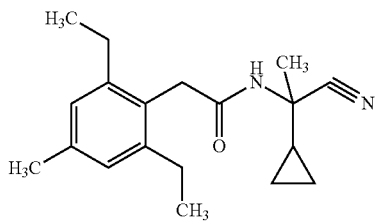 [SMILES: CCc1cc(C)cc(CC)c1CC(=O)NC(C)(C#N)C1CC1]

1.3 g of 2-amino-2-cyclopropylpropionitrile and 1.64 ml of triethylamine are initially charged in 50 ml of tetrahydrofuran. With ice-cooling, 2.66 g of 2,6-diethyl-4-methylphenylacetyl chloride in 50 ml of tetrahydrofuran are added, and the mixture is stirred for 3 days with monitoring by thin-layer chromatography. The triethylamine hydrochloride is filtered off with suction, the solvent is removed under reduced pressure and the residue is used without further purification for preparing the components D' (route 1).

Yield: 3.65 g (58 of theory)
Component D'
Route 2

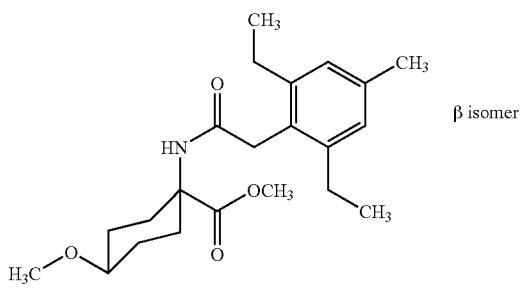

β isomer

At 20° C., 12 g (100.1 mmol) of thionyl chloride are added to 4.13 g (20 mmol) of 2,6-diethyl-4-methylphenylacetic acid in 20 ml of toluene. The mixture is stirred under reflux for 2 h and the solvent is distilled off. The residue is dissolved in 20 ml of tetrahydrofuran and, at 0 to 5° C., added dropwise to a suspension of 4.48 g of methyl 1-amino-4-methoxycyclohexanecarboxylic hydrochloride (0.020 mol) and 6.1 ml (44 mmol) of triethylamine and 100 ml of tetrahydrofuran.

The mixture is stirred at 40° C. for 1 h (monitored by TLC). The solvent is removed using a rotary evaporator. The residue is purified by column chromatography on silica gel (hexane: ethyl acetate, 2:1).

Yield: 5.9 g (72% of theory), m.p. 113° C.

Example I-a-1

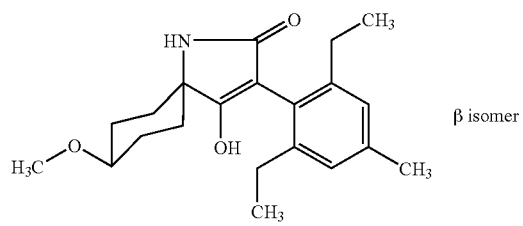

β isomer

At 60° C., 5.7 g of component D' (route 2) in 15 ml of dimethylactamide are added to 3.9 g of potassium tert-butoxide in 20 ml of dimethylacetamide. The mixture is stirred at 80° C. and the reaction is monitored by TLC. The reaction solution is added to 200 ml of ice-water, the pH is adjusted to 2 using concentrated hydrochloric acid and the precipitate is filtered off with suction. The precipitate is purified using methyl tert-butyl ether/hexane.

The product is purified by column chromatography on silica gel (dichloromethane; ethyl acetate, 3:1).

Yield: 5 g (97% of theory)

Preparation of 2,6-Diethyl 4-Methylphenyl Acetic Acid

Component K

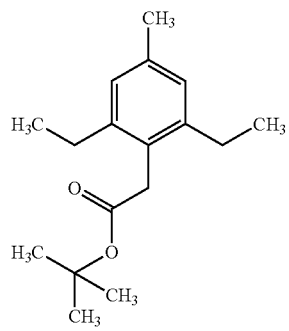 [SMILES: CCc1cc(C)cc(CC)c1CC(=O)OC(C)(C)C]

At 15° C., 5.6 g of tert-butyl acetate were added to 57.2 mmol of a freshly prepared lithium dicyclohexylamide solution. During the addition, the temperature increased from 15° C. to 25° C.

After 10 min, a degassed mixture of 10 g of 2,6-diethyl-4-methylbromobenzene and 0.253 g of bis(dibenzylideneacetone)palladium and 0.089 g of tri-tert-butylphosphine as a 0.5 molar solution in toluene was added. Over a period of 30 min, the temperature increased to 35° C., and over a period of half an hour, the temperature then cooled to 28° C. The reaction mixture was put into a mixture of 10 ml of hydrochloric acid and 200 ml of water, and 400 ml of dichloromethane were added. After 30 min of stirring, the solid was separated off and washed with dichloromethane. The organic phase was removed from the mother liquor and dried with magnesium sulfate. Column filtration on silica gel using ethyl acetate/n-heptane 1:6 gave 12.1 g of product. The viscous oil was reacted further without further purification.

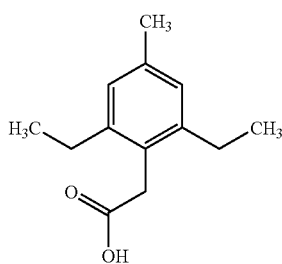

At room temperature, 12 g of component K were stirred in 100 ml of formic acid for 2 h. The mixture was then poured into 400 ml of ice-water and stirred for 30 min, and the solid formed was filtered with suction. For drying, the residue was taken up in dichloromethane and this solution was dried with magnesium sulfate. After concentration, the residue was digested in a little n-heptane and filtered off with suction. This gave 8.2 g of 2,6-diethyl-4-methylphenylacetic acid, which corresponds to a total yield of 90% over all steps. M.p. 124° C.

2,6-Diethyl-4-methylphenylacetic acid

Under an atmosphere of argon, 20.0 g of 2,6-diethyl-4-methylphenylmalodinitrile (94.2 mmol), known from WO 00/78712, are heated in a mixture of 128 g of concentrated sulfuric acid and 48 ml of water at 140° C. for 24 h. After cooling, the mixture is repeatedly extracted with dichloromethane and the extracts are washed twice with water, dried (sodium sulfate) and concentrated. This gives 18.8 g of colorless crystals of melting point 116 to 117° C.

$^1$H-NMR (CDCl$_3$, 300 MHz): δ=1.19 (t, 6H), 2.28 (s, 3H), 2.60 (q, 4H), 3.73 (s, 2H), 6.90 (s, 2H)

Methyl 2,6-diethyl-4-methylphenylacetate 1 ml of concentrated sulfuric acid is added to 18.0 g (87.3 mmol) of 2,6-diethyl-4-methylphenylacetic acid and 300 ml of absolute methanol, and the mixture is heated at reflux for 4 h. After cooling, the mixture is extracted with ethyl acetate, the extracts are washed with water in sodium carbonate solution and dried (magnesium sulfate) and the solvent is distilled off. This gives 18.37 g of (95%) of the desired product as a colorless oil.

$^1$H-NMR (CDCl$_3$, 300 MHz): δ=1.20 (t, 6H), 2.32 (s, 3H), 2.62 (1, 4H), 3.67 (s, 3H), 2.72 (s, 2H), 6.93 (s, 2H)

USE EXAMPLES

Example A

1. Herbicidal Pre-Emergence Action

Seeds of monocotyledonous and dicotyledonous weed and crop plants are placed in sandy loam in wood fiber pots and covered with soil. The test compounds, formulated in the form of wettable powders (WP), are then, as an aqueous suspension with a water application rate of 600 l/ha (converted), with 0.2% of wetting agent added, applied to the surface of the covering soil in various dosages.

After the treatment, the pots are placed in a greenhouse and kept under good growth conditions for the test plants. The visual assessment of the emergence damage on the test plants is carried out after a trial period of 3 weeks by comparison with untreated controls (herbicidal effect in percent (%): 100% effect=the plants have died, 0% effect=like control plants).

In addition to the examples explicitly mentioned, the following compounds, at an application rate of 320 g/ha, show an activity of ≧80% against *Avena sativa, Lolium multiflorum* and *Setaria viridis*: I-a-8, I-a-9, I-b-5, I-b-13, I-b-14, I-c-3.

2. Herbicidal Post-Emergence Action

Seeds of monocotyledonous and dicotyledonous weed and crop plants are placed into sandy loam in wood fiber pots, covered with soil and cultivated in a greenhouse under good growth conditions. Two-three weeks after sowing, the test plants are treated at the one-leaf stage. The test compounds, formulated as wettable powders (WP), are then, in various dosages with a water application rate of 600 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=the plants have died, 0% effect=like control plants).

In addition to the examples explicitly mentioned, the following compounds, at an application rate of 320 g/ha, show an activity of ≧80% against *Avena sativa, Echinochloa crusgalli, Lolium multiflorum* and *Setaria viridis*: I-a-2, I-a-4, I-a-8, I-a-10, I-b-3, I-b-4, I-b-5, I-b-6, I-b-7, I-b-8, I-b-11, I-b-13, I-b-14, I-c-3, I-c-4, I-c-5, I-c-6.

| | Greenhouse | g of a.i./ha | *Alopecurus* | *Avena fatua* | *Lolium* | *Setaria* | *Veronica* |
|---|---|---|---|---|---|---|---|
| Ex. No. I-b-1 | post-emergence | 80 | 100 | 100 | 100 | 100 | 80 |

| | Greenhouse | g of a.i./ha | *Alopecurus* | *Echinochloa* | *Lolium* | *Setaria* | *Veronica* |
|---|---|---|---|---|---|---|---|
| Ex. No. I-c-2 | pre-emergence | 80 | 90 | 100 | 100 | 90 | — |
| | post-emergence | 80 | 100 | 100 | 100 | 100 | 80 |

| | Greenhouse | g of a.i./ha | *Alopecurus* | *Avena fatua* | *Echinochloa* | *Lolium* | *Setaria* |
|---|---|---|---|---|---|---|---|
| Ex. No. I-c-1 | pre-emergence | 80 | 100 | 60 | 100 | 100 | 100 |
| | post-emergence | 80 | 100 | 90 | 100 | 100 | 100 |

-continued

| Greenhouse | | g of a.i./ha | Alopecurus | Avena fatua | Lolium | Setaria | Veronica |
|---|---|---|---|---|---|---|---|
| Ex. No. | pre-emergence | 320 | 100 | 90 | 100 | 100 | 100 |
| I-b-2 | post-emergence | 80 | 100 | 100 | 100 | 100 | 70 |

Example B

2. Herbicidal Post-Emergence Action

Seeds of monocotyledonous and dicotyledonous weed and crop plants are placed into sandy loam in wood fiber pots or in plastic pots, covered with soil and cultivated in a greenhouse, during the vegetation period also outdoors outside of the greenhouse, under good growth conditions. Two-three weeks after sowing, the test plants are treated at the one- to three-leaf stage. The test compounds, formulated as wettable powders (WP) or liquid (EC) are, in various dosages with a water application rate of 300 l/ha (converted), with wetting agent (0.2 to 0.3%) added, sprayed onto the plants and the surface of the soil. Three-four weeks after the treatment of the test plants, the effect of the preparations is rated visually in comparison to untreated controls (herbicidal effect in percent (%): 100% effect=the plants have died, 0% effect=like control plants).

Use of Safeners

If it is additionally to be tested as to whether safeners can improve the plant compatibility of test substances in the case of crop plants, the following options are used for applying the safener:

- seeds of the crop plants are, before sowing, dressed with the safener substance (the amount of safener stated in percent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of the test substances on crop plants without or with safener treatment, it is possible to assess the effect of the safener substance.

Container trials with cereal in a greenhouse
Post-emergence treatment

| | Application g of a.i./ha | Summer barley observed (%) |
|---|---|---|
| Example I-a-1 | 50 | 93 |
| | 25 | 60 |
| | 12.5 | 20 |
| Example I-a-1 + mefenpyr | 50 + 100 | 60 |
| | 25 + 100 | 20 |
| | 12.5 + 100 | 10 |
| Example I-c-1 | 25 | 60 |
| | 12.5 | 35 |
| Example I-c-1 + mefenpyr | 25 + 100 | 40 |
| | 12.5 + 100 | 25 |

Mefenpyr 1 day prior to herbicide application 28 days after application

| | Application g of a.i./ha | Summer wheat observed (%) |
|---|---|---|
| Example I-b-1 | 25 | 90 |
| Example I-b-1 + mefenpyr | 25 + 100 | 50 |

28 days after application

| | Application g of a.i./ha | Summer barley observed (%) | Summer wheat observed (%) |
|---|---|---|---|
| Example I-a-2 | 50 | 50 | |
| | 25 | 25 | 80 |
| | 12.5 | | 40 |
| Example I-a-2 + mefenpyr | 50 + 100 | 20 | |
| | 25 + 100 | 10 | 40 |
| | 12.5 + 100 | | 0 |

28 days after application

| | Application g of a.i./ha | Summer wheat observed (%) |
|---|---|---|
| Example I-b-2 | 12.5 | 95 |
| Example I-b-2 + mefenpyr | 12.5 + 100 | 30 |

Example C

*Myzus* Test—(Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) which are infested by all stages of the green peach aphid (*Myzus persicae*) are sprayed with a preparation of active compound of the desired concentration.

After the desired period of time, the activity in % is determined. 100% means that all aphids have been killed, 0% means that none of the aphids have been killed.

In this test, for example, the following compounds of the preparation examples, at 500 g/ha of a.i., show an activity of ≧90% after 5 d: I-a-2, I-a-10, I-a-11, I-b-1, I-b-2.

Example D

*Tetranychus* Test—(OP-Resistance/Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of bean leaves (*Phaseolus vulgaris*) infested by all stages of the greenhouse red spider mite (*Tetranychus urticae*) are sprayed with a preparation of active compound of the desired concentration.

After the desired period of time, the activity in % is determined. 100% means that all spider mites have been killed, 0% means that none of the spider mites have been killed.

In this test, for example, the following compounds of the preparation examples, at application rates of 100 g/ha of a.i., show an activity of ≧70% after 5 d: I-a-4, I-b-1, I-b-2, I-c-3, I-c-4, I-c-7.

Example E

*Meloidogyne* Test—(Spray Treatment)

| Solvent: | 80 parts by weight of acetone |

To produce a suitable preparation of active compound, 1 part by weight of active compound is mixed with the stated amounts of solvent, and the concentrate is diluted with water to the desired concentration.

Vessels are filled with sand, solution of active compound, *Meloidogyne incognita* egg/larva suspension and lettuce seeds. The lettuce seeds germinate and the plants develop. On the roots, galls are formed.

After the desired period of time, the nematicidal activity is determined in % by the formation of galls. 100% means that no galls have been found; 0% means that the number of galls on the treated plants corresponds to that of the untreated control.

In this test, for example, the following compounds of the preparation examples, at an application rate of 20 ppm of a.i., show an activity of ≧70% after 14 d: I-b-2.

Example F

*Phaedon* Test (PHAECO Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; =% means that none of the beetle larvae have been killed.

In this test, for example, the following compounds of the preparation examples, at application rates of 500 g/ha of a.i., show an activity of ≧80% after 7 d: I-a-2, I-a-11, I-b-1, I-b-2.

Example G

Critical Concentration Test/Soil Insects—Treatment of Transgenic Plants

| Test insect: | *Diabrotica balteata* - larvae in the soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l) matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example H

*Heliothis virescens* Test—Treatment of Transgenic Plants

| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco butterworm *Heliothis virescens* while the leaves are still moist.

After the desired period of time, the kill of the insects is determined.

The invention claimed is:

1. A process for preparing 2,6-diethyl-4-methylphenylacetic acid, comprising reacting 2,6-diethyl-4-methylphenylmalononitrile with an acid, optionally in the presence of a diluent.

2. The method according to claim 1, wherein said acid is a mineral acid.

3. The method according to claim 2, wherein said acid is concentrated sulfuric acid.

* * * * *